United States Patent
Chiavetta et al.

(10) Patent No.: US 7,129,819 B2
(45) Date of Patent: Oct. 31, 2006

(54) MODULAR DRUG RELEASING SYSTEM

(76) Inventors: James N. Chiavetta, 710 Hampton Trace La., Alpharetta, GA (US) 30004; M. Neil Frazer, 109 Greyfriars La., Cary, NC (US) 27511; Chris Morgan, 404 Billings Farm Dr., Canton, GA (US) 30115; Jack Tipsword, 3994 Paloverde Dr., Kennesaw, GA (US)

( * ) Notice: Subject to any disclaimer, the term of this patent is extended or adjusted under 35 U.S.C. 154(b) by 371 days.

(21) Appl. No.: 10/418,800

(22) Filed: Apr. 18, 2003

(65) Prior Publication Data

US 2003/0231119 A1    Dec. 18, 2003

Related U.S. Application Data

(63) Continuation-in-part of application No. 09/210,824, filed on Dec. 14, 1998, now abandoned.

(51) Int. Cl.
    *G08B 1/00*    (2006.01)
(52) U.S. Cl. ............................. 340/309.16; 340/309.7; 368/10
(58) Field of Classification Search ........... 340/309.15, 340/573.1, 309.4, 309.5, 309.16, 309.7; 221/2, 221/3, 15; 206/531; 368/10
    See application file for complete search history.

(56) References Cited

U.S. PATENT DOCUMENTS

| | | | |
|---|---|---|---|
| 4,768,176 A | | 8/1988 | Kehr et al. .................... 368/10 |
| 5,408,442 A | * | 4/1995 | Hepp ........................... 367/135 |
| 5,408,443 A | * | 4/1995 | Weinberger .................. 368/10 |
| 5,724,021 A | * | 3/1998 | Perrone .................... 340/309.7 |
| 6,084,504 A | * | 7/2000 | Rosche et al. ........... 340/309.7 |
| 6,102,855 A | | 8/2000 | Kehr et al. ................. 600/300 |
| 6,194,995 B1 | * | 2/2001 | Gates ...................... 340/309.7 |
| 6,581,797 B1 | * | 6/2003 | McKinney et al. ............ 221/7 |
| 6,594,549 B1 | * | 7/2003 | Siegel ........................ 700/241 |

* cited by examiner

*Primary Examiner*—Daryl C Pope
(74) *Attorney, Agent, or Firm*—Thomas, Kayden, Horstemeyer & Risley, LLP

(57) ABSTRACT

Disclosed are systems and methods for processing the releasing and/or dispensing of releasable items, particularly pills, capsules, tablets, medications, and drugs. In one embodiment, a system for processing the releasing and/or dispensing releasable items includes a releasing unit configured to verify whether a cartridge is authorized for usage with a releasing unit. The releasing unit is further configured to send data corresponding to the releasable items and the activities of the items via a network and/or telephone line. The system further includes a central-computing device configured to receive the data via the network and/or telephone line and provide a database of the data to a provider, i.e., pharmacist. In one embodiment, a method for processing the releasing and/or dispensing of releasable items includes verifying whether a cartridge is authorized for usage with a releasing unit, gathering data corresponding to the releasable items from the cartridge, determining whether to release the releasable items to a user in accordance to the gathered data, recording data corresponding to the activities of the medication in a memory in the releasing unit, sending the data from the releasing unit to a central-computing device via a network and/or telephone line, wherein the central-computing device provides a database of the activities data and sends the database to a provider.

49 Claims, 15 Drawing Sheets

MODULAR DRUG RELEASING SYSTEM

CROSS-REFERENCE TO RELATED APPLICATION

This application is a Continuation-in-Part of U.S. utility application entitled, "Modular Drug Dispensing System," having Ser. No. 09/210, 824 filed Dec. 14, 1998 now abandoned, which is entirely incorporated herein by reference.

REFERENCE TO RELATED DOCUMENTS

The Utility Patent Application is based on the concept disclosed in Disclosure Document No. 430,261 filed Dec. 27, 1997 by Neil Frazer, entitled "Medicab."

TECHNICAL FIELD

The present invention relates to releasing items, such as pills, capsules, tablets, medications, and drugs. More particularly, the disclosure relates to systems and methods for processing the releasing and/or dispensing of releasable items in accordance with the information provided by a pharmacist.

BACKGROUND OF THE INVENTION

Typically, a patient that is prescribed a medication reads the instructions on the prescription bottle and other written documents to inform the patient when and how much medication to take during a period of time. Sometimes, the patient needs a refill of the medication and must remember to place an order with a pharmacist a few days before the patient runs out of medication. The pharmacist places an order for the medication whenever the patient places the order. If the patient does not place the order, the pharmacist simply does not order the medication. Some problems that arise from this scenario are that the patient sometimes forgets to take his medication at the proper time, the patient has to physically go to a pharmacist store to place an order for his medication, the medication is not readily accessible to the patient when the patient places an order for his medication, etc.

In addition, there are more medications available now than before to treat various diseases, such as kidney failure, diabetes, cancers, etc. Some of these illnesses require multiple medications to treat the illness. For example, a patient with kidney failure may be required to take medications for high blood pressure, medication for controlling his blood sugar level, and other medications to substitute the functions of the kidney. The management of dispensing the medication from the pharmacist to the patient and releasing the medication to the patient has become difficult and at times overbearing. Self management of medication is especially difficult for elderly patients who may have multiple medications that must be taken on different time schedules.

From the above, it can be appreciated that it would be desirable to have a reliable system and method for processing the releasing and/or dispensing of releasable items, i.e., pills, capsules, tablets, medications, and drugs.

SUMMARY OF THE INVENTION

Disclosed are systems and methods for processing the releasing and/or dispensing of releasable items, particularly pills, capsules, tablets, medications, and drugs. Typically, a patient is prescribed a medication from a doctor after the doctor has examined the patient. The prescription is given to a pharmacist who then fills a cartridge with the medication. The pharmacist also programs an electronic chip coupled to the cartridge to include information that is necessary to inform the patient about the medication and to allow the cartridge to work properly with a releasing unit owned by the patient. Once the cartridge is programmed, this information is transmitted to a central-computing device that prepares a database that includes the activity of the medication. For example, the activities that relates to the medication include when the medication was released from the releasing unit, how much medication was released, who released the medication, etc.

The cartridge is then inserted into a slot of the releasing unit owned by the patient. The cartridge includes a case and a carousel rotatably received in the case about a central axis of rotation. The carousel has a series of compartments each for storing at least one medication. The compartments are in a circular array about the axis of rotation of the carousel and each compartment has a releasing opening to facilitate the releasing of medication from the releasing unit. The case includes a discharge opening that is aligned with the circular array of the compartments for registering with the releasing openings of each of the compartments in sequence as the carousel rotates about a central axis of rotation in the case. The case also has an opening therein that a releasing engine may gain access and couple against the carousel for rotating the carousel so that the releasing openings of the carousel register in sequence with the discharge opening of the case.

Once the casing is inserted into the slots of the releasing unit, the releasing unit verifies whether the electronic chip contains data that authorizes usage of the cartridge with the releasing unit. If the electronic chip does not contain authorized data, the releasing unit notifies the patient and/or caretaker by way of a user interface, i.e., a LCD display, button, audio speakers, and light components.

If the electronic chip contains authorized data, the releasing unit then gathers data corresponding to the medication from the electronic chip. As explained above, the medication may be comprised of data of when a patient can take the medication, and how much medication a patient can take at a time. The releasing unit uses a processor and a clock to determine when to release the medication and how much medication to be released in accordance with the gathered data.

The releasing unit then notifies the patient that the medication should be released from the releasing unit. The notification, for instance, may be displayed on an LCD, flashed and blinked with light components, beeped with audio speakers, and paged with a pager/modem. The patient presses a release button to release the medication from the releasing unit. The releasing unit responds by rotating the carousel in the case of the cartridge such that the medication in the carousel is released through a discharge opening of the case and into a drawer that a patient pulls out of the releasing unit to access the medication. If the patient is not able to push the release button, a caregiver may operate and audio speakers can be disabled by software selection.

It should be noted that releasing unit can remind the patient/caregiver/user to administer non-releasable items, such as eye drops, checking blood pressure or applying medication cream. The pharmacist programs the electronic chip coupled to the cartridge to include information that is necessary to inform the patient/caregiver/user about the non-releasable items and to allow the cartridge to work properly with a releasing unit owned by the patient. The releasing unit functions similarly to cartridge with releasable items except that the non-releasable items are not in the cartridge and the items are not released from the releasing unit. The releasing unit provides a reminder to administer the non-releaseable items to the patient/caregiver/user.

The releasing unit records the activities of the medication, such as when the medication was released, when the medication was not released, how much medication was released and who released the medication. The information in relation to the activities of the medication is transmitted to a central-computing device via a network and/or telephone line. The central computing provides a database that corresponds to the information on the medication and the activities of the medication. The releasing unit may transmit the data to the central-computing device on a periodic basis, such as hourly, daily, weekly, or monthly, or on demand (also known as "forced dial").

The central-computing device gathers the data transmitted from the releasing unit and provides a database of the data. The central-computing device may generate a Medication Administration Report (MAR) based on the data collected by the central-computing device. The central-computing device may transmit the database (or an electronic MAR) to a provider-computing device via the network and/or telephone line. The provider-computing device receives the database via the network and/or telephone line and provides the database to the pharmacist. The pharmacist may obtain the database corresponding to the information on the medication and the activities of the medication from the provider-computing device and determines whether to refill the cartridge. If the pharmacist determines that the patient needs a refill, the pharmacist then refills the cartridge and begins the entire process again.

In one embodiment, a system for processing the releasing and/or dispensing releasable items includes a releasing unit configured to verify whether a cartridge is authorized for usage with a releasing unit. The releasing unit is further configured to send data corresponding to the releasable items and the activities of the items via a network and/or telephone line. The system further includes a central-computing device configured to receive the data via the network and/or telephone line and provide a database of the data to a provider, i.e., pharmacist.

In one embodiment, a method for processing the releasing and/or dispensing of releasable items includes verifying whether a cartridge is authorized for usage with a releasing unit, gathering data corresponding to the releasable items from the cartridge, determining whether to release the releasable items to a user in accordance to the gathered data, recording data corresponding to the activities of the medication in a memory in the releasing unit, sending the data from the releasing unit to a central-computing device via a network and/or telephone line, wherein the central-computing device provides a database of the activities data and sends the database to a provider.

BRIEF DESCRIPTION OF THE DRAWINGS

The disclosed systems and methods can be better understood with reference to the following drawings. The components in the drawings are not necessarily to scale.

DETAILED DESCRIPTION OF THE PREFERRED EMBODIMENT

Disclosed herein are systems and methods to which releasable items, i.e., pills, capsules, tablets, medications, and drugs, can be released and/or dispensed. In particular, the releasing of the releasable items from a releasing unit can be controlled with a releasing unit and a cartridge, wherein the cartridge includes an electronic chip that contains data allowing the releasing unit to process the data and to determine when and how many releasable items to be released. The dispensing of the releasable items from a provider, i.e., pharmacist, can be achieved by transmitting a database containing information corresponding to the releasable items and the activities of the items with the releasing unit. Example systems are first discussed with reference to the figures. Although the systems are via a network and/or telephone line to a provider-computing device from a central-computing device, the provider may access the database in the provider-computing device and determine whether to provide a new supply of releasable items to the user. After the example system has been described, examples of operation of the system are provided to explain the manner in which the process of releasing and/or dispensing releasable items i.e., pills, capsules, tablets, medications, and drugs, can be achieved.

Figure 1:
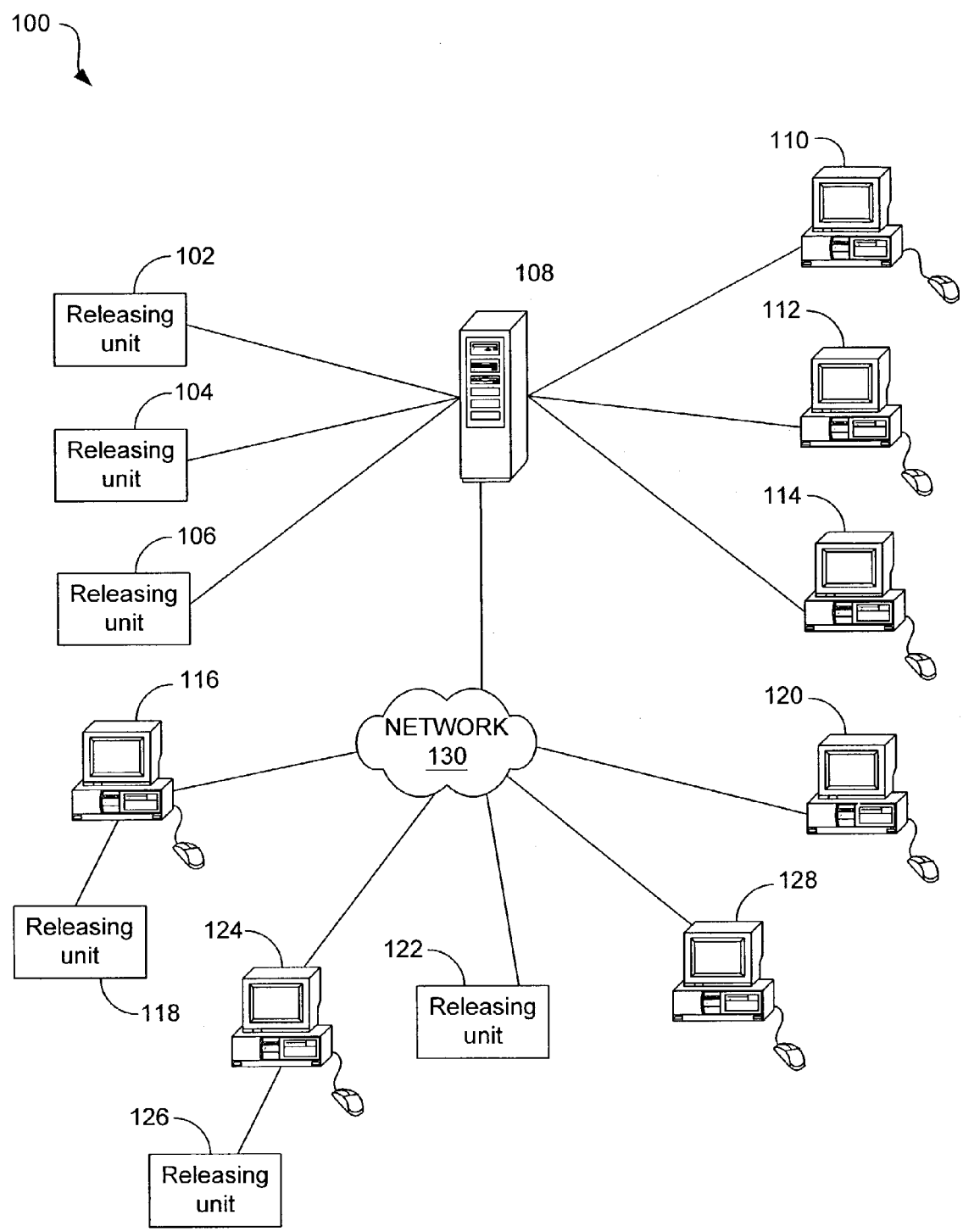
FIG. 1 is a schematic view of an embodiment of a system through which the releasable items can be released and/or dispensed.

Referring now in more detail to the figures in which like reference numerals identify corresponding parts, FIG. 1 illustrates an example system 100 in which releasable items can be released. As indicated in this Figure, the system 100 generally comprises one or more releasing units 102, 104, 106, 118, 122, 126, a central-computing device 108, and one or more provider-computing devices 110, 112, 114, 120, and 128. As shown in FIG. 1, one or more releasing units 102, 104, 106 may communicate with the central-computing device 108 via a telephone line. The central-computing device 108 also communicates with the provider-computing device 110, 112, 114 via telephone lines.

As indicated in FIG. 1, the releasing unit 118, 126 may communicate with the user-computing device 116, 124, which communicates to the central-computing device 108 via the network 130. The provider-computing devices 120, 128 may also communicate to the central-computing device 108 via the network 130. As shown in FIG. 1, the user-computing devices 116, 124 and provider-computing devices 110, 112, 114, 120, 128 can, for instance, comprise desktop personal computers (PC) or Macintosh computers. The user-computing devices 116, 124 are typically located in a clientele location, such as a hospital, a nursing home, an assisted living home, and a patient's home. The provider-computing devices are typically located in a pharmacist store. In addition, the releasing units 122 may communicate to the central-computing device 108 via the network 130 without communicating through user-computing devices 116, 124. In this regard, the releasing unit 122 may, for example, include an embedded web server that supports communication between the releasing unit 122 and the central-computing device 108 via the generation of one or more web pages.

The network 130 may comprise one or more sub-networks that are communicatively coupled to each other. By way of example, these networks include one or more local area networks (LANs) and/or wide area networks (WANs).

Figure 2:
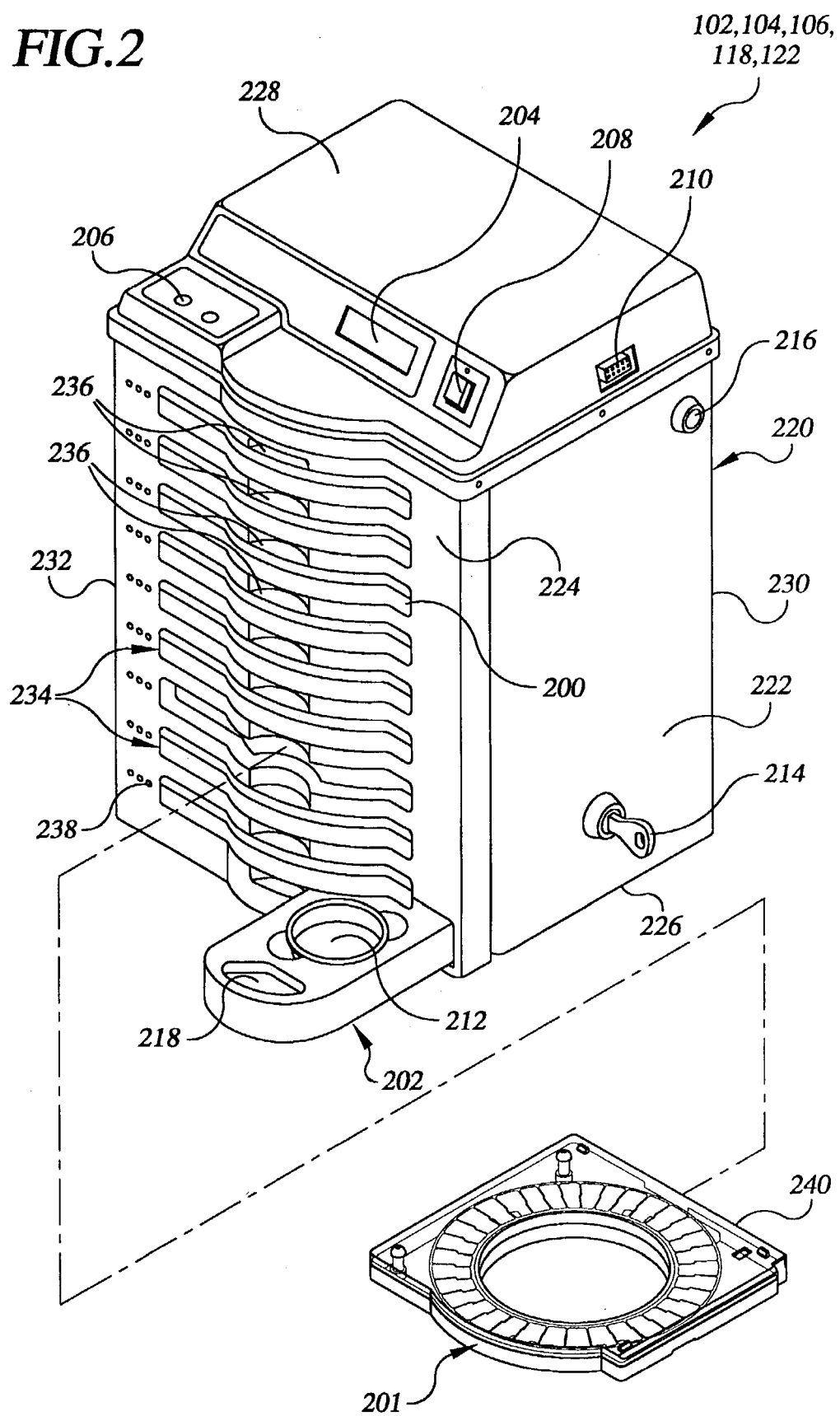
FIG. 2 is a perspective view of an embodiment of the releasing unit as shown in FIG. 1.

FIG. 2 is a perspective view of an embodiment of the releasing units 102, 104, 106, 118, 122, 126 as shown in FIG. 1. As shown in FIG. 2, the releasing unit comprises a housing 220 that includes side walls 222, 224, 230, and 232. The housing further includes a top wall 228 and a bottom wall 226. Side wall 224 further includes slots 234 such that cartridges 200, 201 may be inserted into the slots for releasing releasable items. Each slot 234 further includes a viewable section 236 that is concave such that a user may see the releasable items, i.e., pills, capsules, tablets, medications, and drugs, contained in the translucent cartridges 200, 201.

Side wall 224 further includes at least one light component 238 that indicates to the user whether the cartridge is intended for usage with the releasing unit, whether the releasable items was released to the user, whether the user selected the proper cartridge when releasing the items, etc. The light component 238 may change colors. For instance, a steady green light indicates that the cartridge was installed and operating properly; a steady yellow light indicates that the cartridge is empty or there is a problem with the cartridge being installed improperly; a flashing green light indicates that the cartridge was selected or that the items should be released shortly, etc.

As further shown in FIG. 2, the releasing units 102, 104, 106, 118, 122, 126 further include a drawer 202 that the releasable items, i.e., pills, capsules, tablets, medications, and drugs, are released in when the drawer 202 is closed. The user obtains the items by pulling the drawer 202 open. The drawer 202 includes a cup 212 that is placed on top of the cup holding portion of the drawer 202. The cup holding portion further includes at least one finger aperture for a user to partially insert his finger(s) into the cup holding portion and grip the cup 212. The drawer 202 further includes a handle 218 which may simply be an indentation that is formed on top of the drawer or a raised member coupled to the drawer 202. The handle 218 on the drawer 202 may be formed in various ways known in the industry for closing and opening the drawer 202. The drawer 202 may slide in and out of the releasing unit. The releasing unit may sense whether the drawer 202 is opened or closed, and may record into memory when the user opened the drawer 202 to obtain the releasable items, i.e., pills, capsules, tablets, medications, and drugs. The drawer may include a lock 214 operated by a key, or it may be an electronic lock operated without a key (not shown).

The releasing unit further includes a cartridge lock 216 for locking or unlocking the cartridge, shown in FIG. 2. The releasing unit further includes a user interface for interacting with the user to facilitate releasing releasable items to the user. The user interface may include an audio speaker (not shown), a release button 208, a display 204 (i.e., LCD display), and functional buttons 206. Buttons 206 allow the user to select the cartridges in the releasing unit, menus and functionality (such as advancing the items, pausing the activities of the releasing unit, entering access information, releasing the releasable items, etc.) In addition, the releasing unit further includes a communication port 210 to communicate with the central-computing device 108 via the network 130 and/or telephone line. Further, the releasing unit may include a back-up power source (not shown) that provides power to the unit when the main power source is disconnected.

Figure 3:
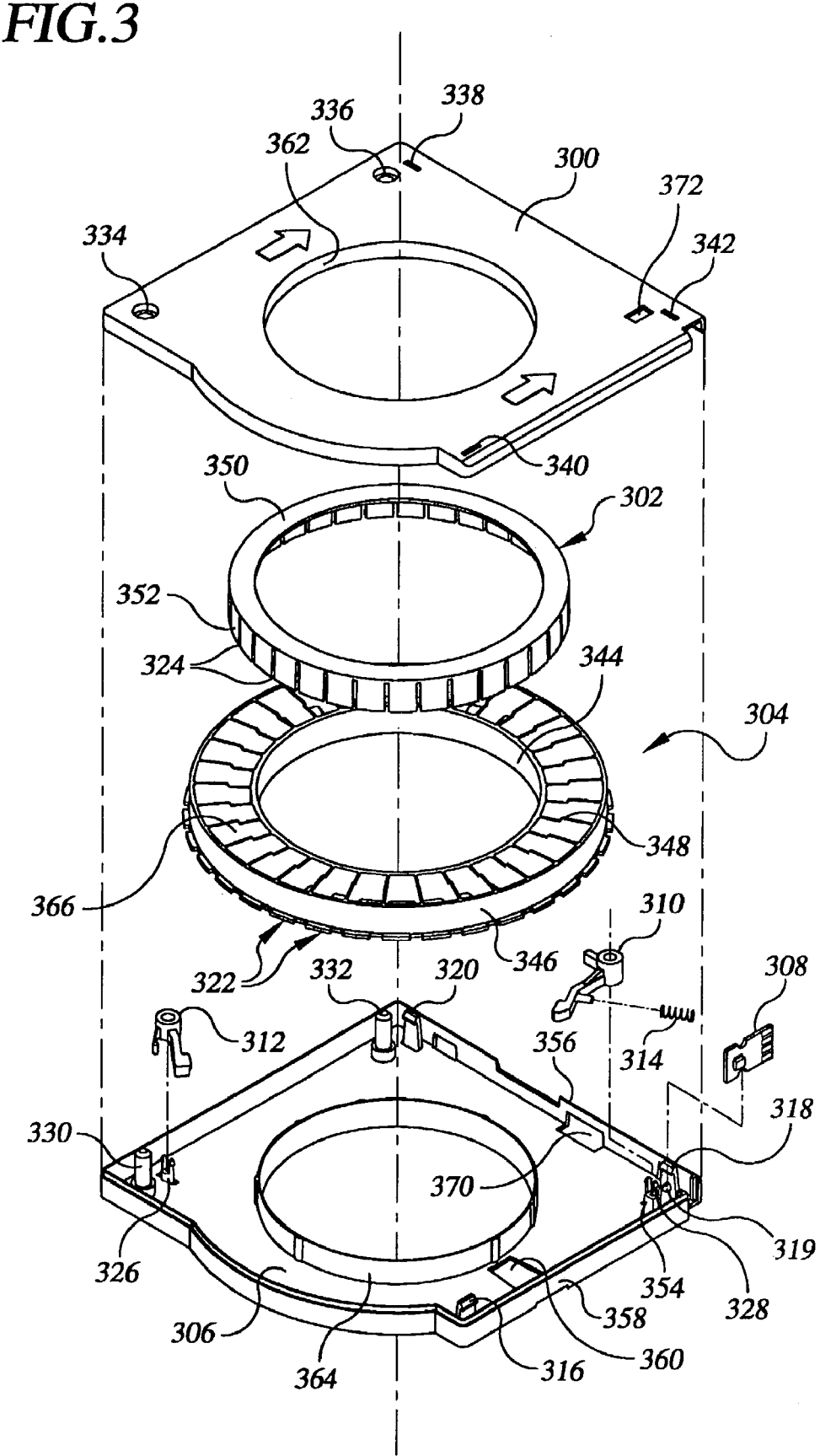
FIG. 3 is a perspective view of an embodiment of the cartridge as shown in FIG. 2.

FIG. 3 is a perspective view of an embodiment of the cartridge 200, 201 as shown in FIG. 2. The cartridge 200, 201 comprises a case 240 that includes a top portion 300 and a bottom portion 306. The top portion 300 includes a top annular wall 362 and the bottom portion 306 includes a bottom annular wall 364. The annular walls 362, 364 are coupled together to form a central axis of rotation such that carousel 304 is rotably received in the case 240. The bottom portion 306 may further include a discharge opening 360 where the releasable items are released. The bottom portion 306 may further include a releasing engine engagement opening 370 that a releasing engine, shown in FIG. 5, may gain access to carousel 304 and rotate the carousel 304.

The top and bottom portions 300, 306 are coupled together via clips 316, 318, 320. The clips 316, 318, 320 may be comprised of a wedge-shaped head. The clips in the bottom portion of 306 of the case 240 couple with latching members 338, 340, 342. The latching member extends downward from the inside of the top portion 300 of the case 240. The latching member may include three side walls and a bottom wall. The latching member may further include a side opening and a top opening. The side opening allows the wedge-shaped head of the clips 316, 318, 320 to clip onto the latching mechanism that is coupled to the top portion 300 of the case. The top opening of the latching member allows the user to slide a paper clip or other like devices between the wedge-shaped head of the clip and a side wall of the latching mechanism such that the clip may be pried away from the latching mechanism to unclip the top portion 300 and bottom portion 306 of the case 240.

As further shown in FIG. 3, the case 240 may further include posts 320, 332 and post-engaging holes 334, 336. The posts 330, 332 on the bottom portion 306 of the case 240 couple with post-engaging holes 334, 336 on the top portion 300 of the case 240. The posts 330, 332 and the holes 334, 336 facilitates coupling together the top portion 300 and the bottom portion 306 of the case 240 when assembling the cartridge 200, 201. The posts and holes may be positioned anywhere in the cartridge such as on the corner of the case 240 or any area between the corners of the case 240.

As further shown in FIG. 3, the cartridge further includes a carousel 304 that includes a first annular wall 344 and second annular wall 346. The first annular wall 344 is smaller in diameter than the second annular wall 346. The annular walls 344, 346 are coupled to form the carousel via side wall 348. The side walls 348 along with the annular walls 344, 346 forms a compartment to contain or facilitate storing the releasable items, i.e., pills, capsules, tablets, medications, and drugs. The series of compartments are arranged in a circular array about the central axis of rotation of the carousel 304. Each of the compartments includes a release opening 366, which aligns with the discharge opening 360 of the case 240 to facilitate releasing the releasable items. The discharge opening 360 also aligns with the circular array of the compartment for registering with the release opening 366 of each of the compartments in sequence as the carousel rotates.

The carousel 304 further includes radially extending tabs 322. The tabs 322 are coupled to the second annular side wall 346. The tabs 322 facilitate indexing the compartments of the carousel when the releasing unit is in operation. For example, the tabs may be positioned on each and every compartments of the carousel such that the compartment may be indexed as it rotates in the cartridge. A releasing engine (shown in FIG. 5) of the releasing unit includes an indexing device that detects the tabs 322 of each component to determine when to stop rotating the carousel in the cartridge. In this regard, as the carousel turns, the indexing device of the releasing engine provides feedback to the motor to stop rotating the carousel as it senses the next sequential tab on the carousel. The releasing engine rotates the carousel 304 so that the release opening 366 of the carousel register in sequence with the discharge opening 360 of the case 240. The tabs 322 and the releasing engine facilitate releasing releasable item, in the cartridge, i.e., one item per releasing or two items per releasing. The releasing engine is further described in relation to FIG. 5.

The cartridge further includes a partitioning insert as shown in FIG. 3. The partitioning insert 302 partitions the compartment such that the releasable items are positioned in the outer circumference of the carousel 301. The partitioning insert prevents the releasable items from frictionally attaching itself between the side wall 348 of the compartments of the carousel 304. For example, the releasable items may be larger than the inner circumference of the compartment of the carousel 304. In this regard, the releasable item, i.e., pills, capsules, tablets, medications, and drugs, may be stuck to the side walls 348 of the compartment of the carousel 304. The partitioning insert may be comprised of a first portion and a second portion. The first portion may be a flat ring 350, wherein the inner circumference of the flat ring 350 has a slightly larger circumference than the first annular side wall 344 of the carousel 304. The partitioning insert 302 further includes a second portion 352 that is coupled to the outer circumference of the ring 350. The second portion 352 is coupled substantially perpendicular to the flat ring 350. The second portion further includes slots 324, which engages the side walls 348 of the carousel 304, such that the insert 302 may be placed on top of the carousel 304 and partitions the compartments of carousel 304. The second portion having slots 324 enables the side walls 348 of the carousel 304 to slide into the slots 324 of the insert 302. The assembling of the cartridge 200, 201 with partitioning insert 302 is further described in relation to FIG. 7.

As shown in FIG. 3, the cartridge bottom portion 306 further includes locking arms 310, 312, which are coupled to the cartridge bottom portion 306 via spring loaded clips 326, 328. The clips 326, 328 are coupled to the inside portion of the cartridge bottom 306. The locking arms 310, 312 are spring loaded that are either integrated as part of the locking arms, as shown in locking arms 312, or provided with a coiled metal spring 314 and coupled to the locking arm 310. The integrated spring load member of the locking arms 312 couples with the post 330 to push the locking arm against the carousel 304. Similarly, the locking arm 310 couples with the coiled spring 314 such that the combination of the locking arm 310 and spring 314 uses an angled wall formed as part of guiding member 354. In this regard, the locking arm 310 pushes against the carousel 304. As a result, the two locking arms 310, 312 facilitate guiding the carousel as it rotates in the cartridge and aligning the discharge opening 360 of the case 240 with the release opening 366 of the carousel 304. The locking arms 310, 312 also facilitate indexing and/or positioning the releasable items above the opening 360 of the bottom portion 306 for releasing releasable items, i.e., pills, capsules, tablets, medications, and drugs, from the cartridge 304.

The cartridge 304 may also include an electronic chip 308, which includes a PCB board and a memory, such as an E-PROM or EE-PROM. The electronic chip 308 may be programmed to store information provided by the pharmacist, such as when to take the medication (schedule), how to take the medication, the name of the medication, the patient identification number, the facility identification number, etc. The electronic chip 308 may also be programmed to count the movement of the carousel with respect to the case 240.

The chip 308 may be coupled to the cartridge via the memory PCB board clip 319, guiding member 354 and part of the cartridge bottom portion 306. The chip 308 is coupled to the cartridge by sliding the chip 308 into the guiding member 354. The PCB board clip 319 includes a wedge-shaped head, which allows the clip 319 to move away from the chip 308 as it slides down the guiding member 354. The clip 319 clips the chip 308, which rests on the inner surface of the cartridge bottom portion 306. The PCB board clip 319 prevents the chip 308 from moving upward away from the cartridge bottom portion 306. The guiding member 354 not only provides the chip 308 to slide into position, but it also prevents the chip 308 from sliding horizontally toward or away from a clip 319 and toward spring-load clip 328.

The chip 308 is further positioned by using the side walls 356, 358 of the cartridge bottom portion 306. As shown in FIG. 3, opposite from the guiding member 354, the side wall 356 of the cartridge bottom portion 306 includes a right angled member that prevents the chip 308 from moving toward clip 320. The right-angled member further prevents the chip 308 from moving away from the guiding member 354. Further, the PCB board clip 319 also prevents the chip 308 toward clip 320. In addition, the side wall 358 of the bottom portion 306 does not extend fully to the side wall 356, which creates an area that allows the releasing unit to read the programmable readable memory on the chip 308. The side wall 358 protrudes towards the PCB board clip 319 to prevent the chip 308 from moving away from the PCB board clip 319 towards the side wall 358. The combination of the guiding member 354, PCB board clip 319, and the side walls 356 and 358 enables the chip 308 to couple onto the cartridge 200, 201.

Figure 4:
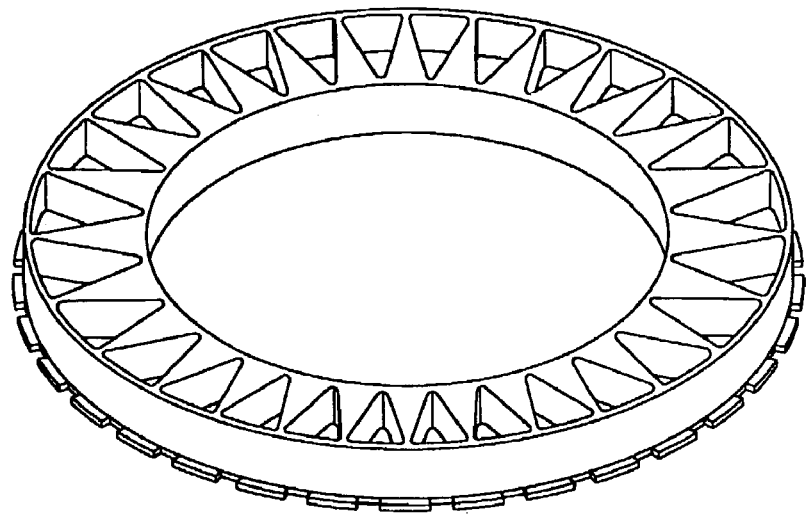
FIG. 4 is a perspective view of an embodiment of a carousel.

The compartment in the carousel 304 may be formed in a variety of shapes, such as a square, rectangle, trapezoid, triangle, or other similar shapes. A triangular shape compartment of the carousel 304 is shown in FIG. 4.

Figure 5:
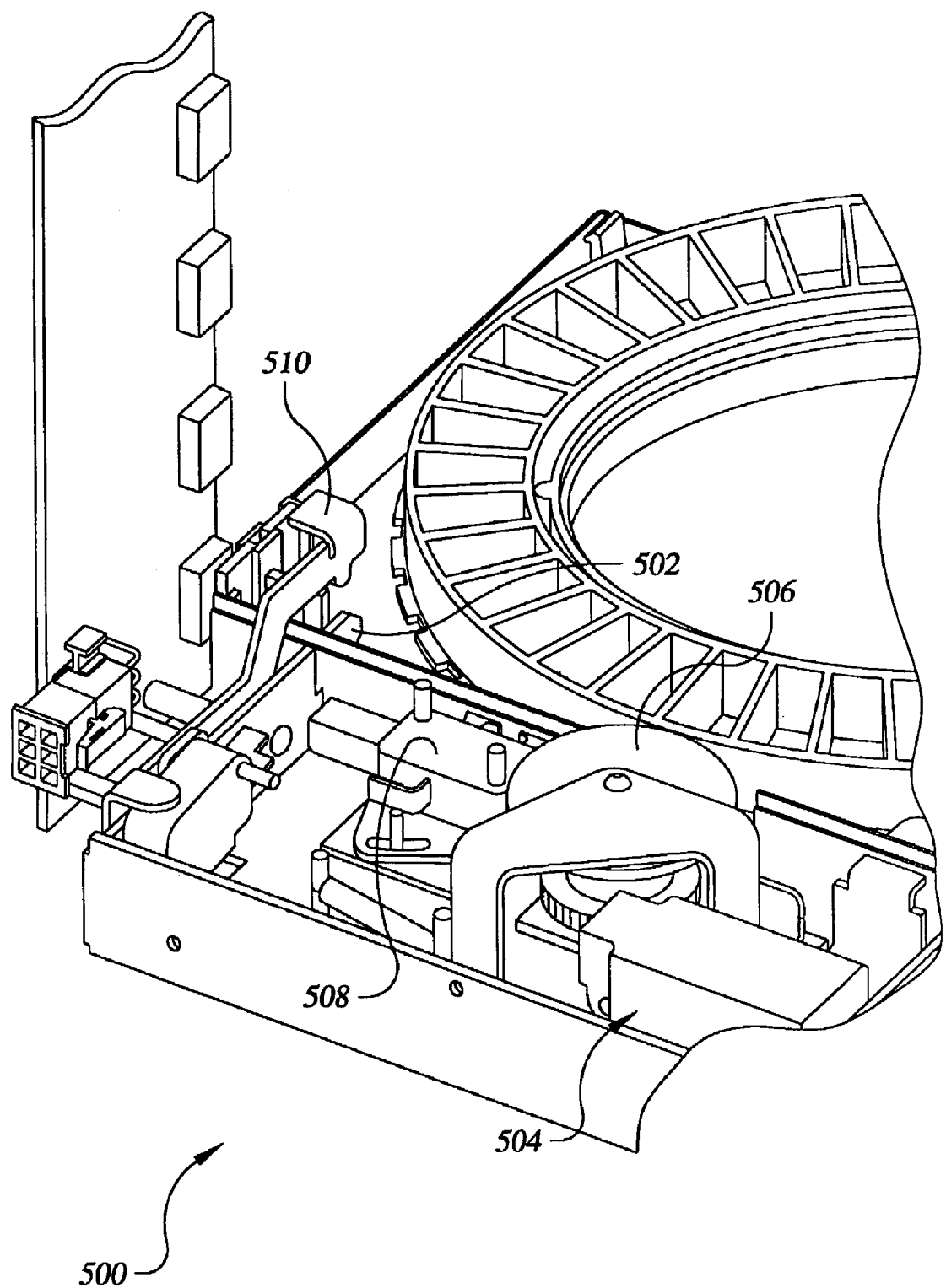
FIG. 5 is a perspective view of an embodiment of the releasing engine that facilitates releasing releasable items from the cartridge.

FIG. 5 is a perspective view of an embodiment of the releasing engine that facilitates releasing releasable items from the cartridge 200, 201. When the cartridge 200, 201 is placed into the releasing unit, the cartridge engages the releasing engine 500, as shown in FIG. 5. The engine 500 may include an unlocking arm 502 that pushes the locking arm 310 (shown in FIG. 2) away from the carousel 304, which allows the carousel 304 to rotate in the cartridge 200, 201. The releasing engine may further include cartridge locking arms 510 that engages lock opening 372 of the top portion 300 of case 240 and locks the cartridge 200, 201 into the releasing unit. The cartridge 200, 201 may automatically be locked to the releasing unit when the cartridge engages the releasing engine 500. The cartridge lock 216, shown in FIG. 2, may unlock the cartridge from the releasing unit by turning a key in the lock 216 and disengaging the cartridge locking arm 510 from the cartridge 200, 201, which can be removed from the releasing unit.

The releasing engine 500 may further include a motor 504 and disc 506 that facilitates rotating the carousel 304. The motor 504 is coupled to the disc 506, which is coupled to the carousel 304. The motor 504 rotates the disc 506, which, in turn, rotates the carousel 304. The engine 500 may further include sensing arm 508 that detects the tabs 322, shown in FIG. 3, to determine when to stop rotating the carousel 304 so that the release openings 366 of the carousel 304 register in sequence with the discharge opening 360 of the case 240.

Figure 8:
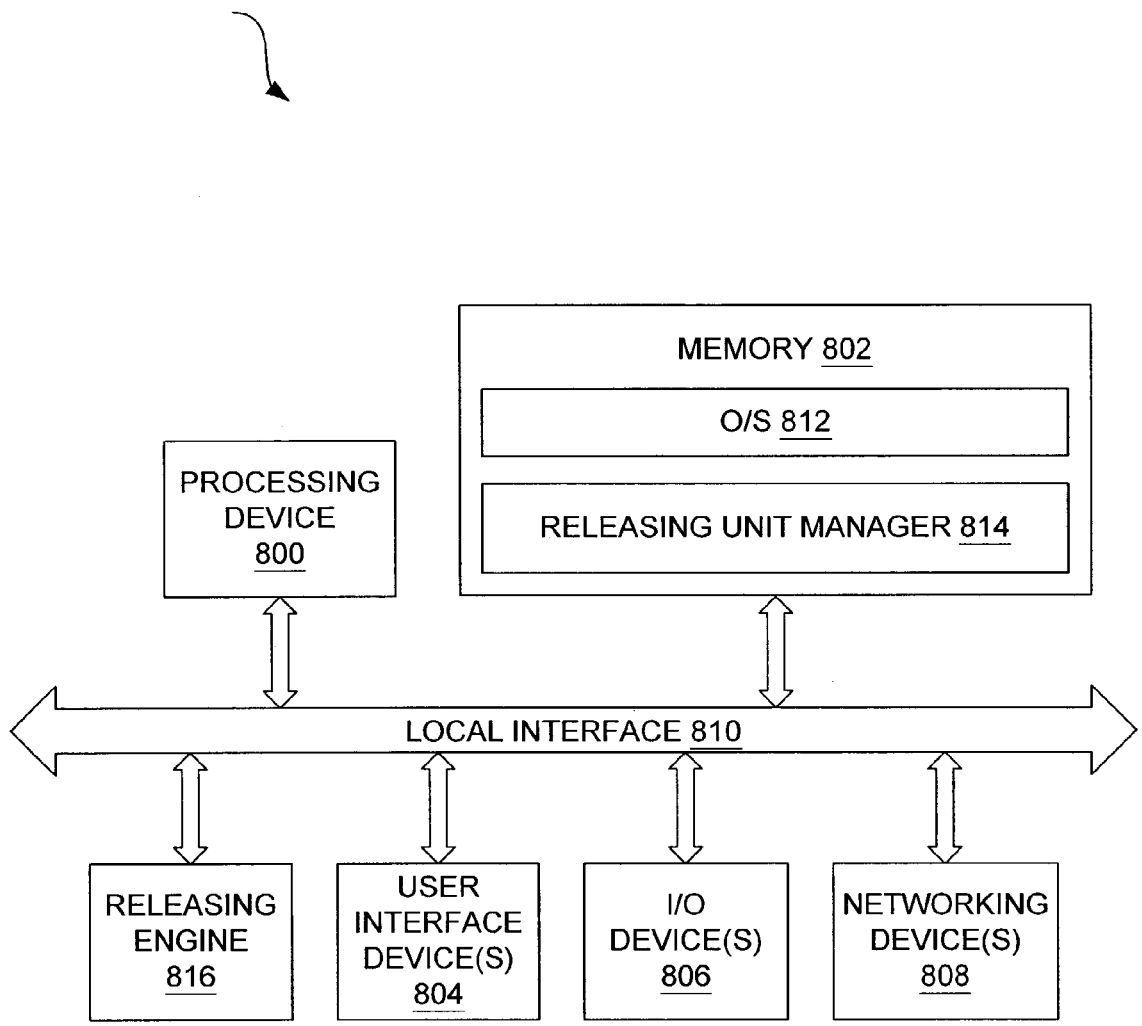
FIG. 8 is a block diagram illustrating an example architecture for the releasing unit as shown in FIG. 1.

As shown in FIG. 5, each of the releasing units includes an interfacing device 512 that allows the processor, shown in FIG. 8, to read/write to the electronic chip 308 of the cartridge. The processor is also coupled to the releasing engine for tracking the movements of the carousel with respect to the housing 220 and determining the number of medication released. The interfacing device 512 is part of the input/output (I/O) devices 806, as further described in relation to FIG. 8.

Figure 6:
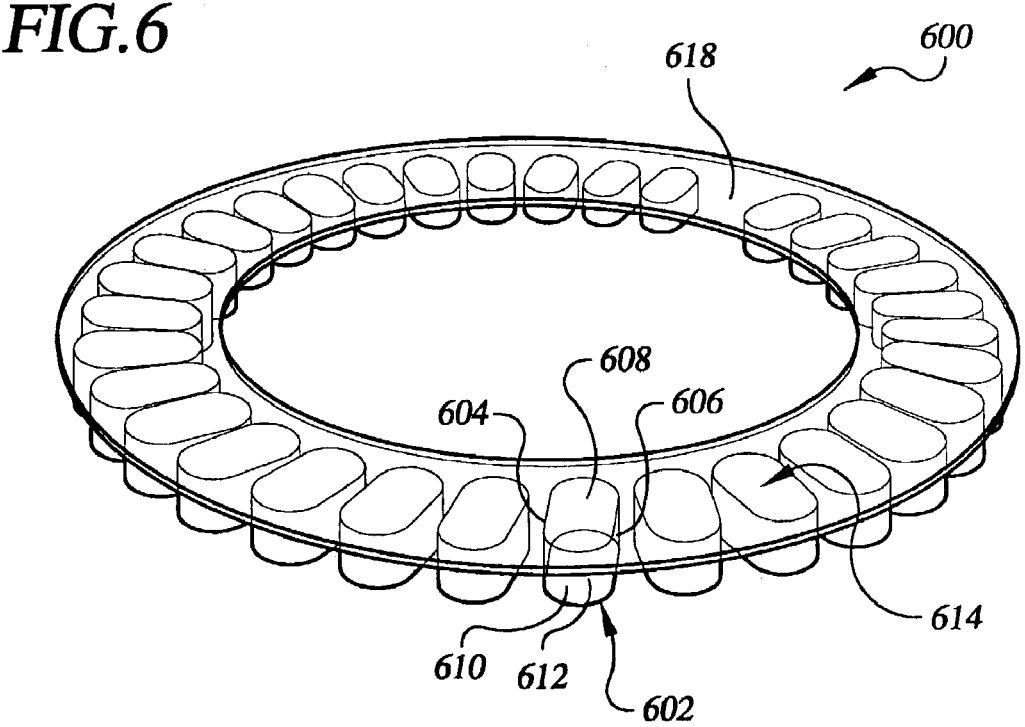
FIG. 6 is a perspective view of an embodiment of a bubble pack that is placed into the cartridge.

FIG. 6 is a perspective view of an embodiment of a bubble pack that may be inserted in the cartridge 200, 201. The bubble pack 600 may include a flat ring 616 and at least one sack 602, which may contain releasable items, i.e., pills, capsules, tablets, medications, and drugs, and are placed in the carousel compartment to facilitate releasing releasable items. The flat ring 616 is coupled to the sack 602 as shown in FIG. 6. The sack 602 may include at least three side walls to form a pyramid-like or cube-like shape. For example, as shown in FIG. 6, the sack includes four side walls 604, 606, 608, 610. The sack further includes a bottom wall 612. The side walls 604, 606, 608, 610 and bottom wall 612 are coupled together such that the sack may be placed in the compartment of the carousel 304. Another example of the sack, which is not shown, may include only three walls and no bottom wall. The three walls are coupled together to form a pyramid-like shape. Another example of the sack 602, which also is not shown, is a cone-like shape. The bubble pack 600 includes an opening 614 in the sack 602, as shown in FIG. 6. Releasable items, i.e., pills, capsules, tablets, medications, and drugs, may be placed through the opening 614 and into the sack 602. Bubble pack 600 may also include an aligning space 618 which allows the assembler of the cartridge to align the aligning space 618 with the opening of the cartridge when assembling the cartridge. The assembling of the cartridge 200, 201 with the bubble pack 600 is further described in relation to FIG. 17.

Figure 7:
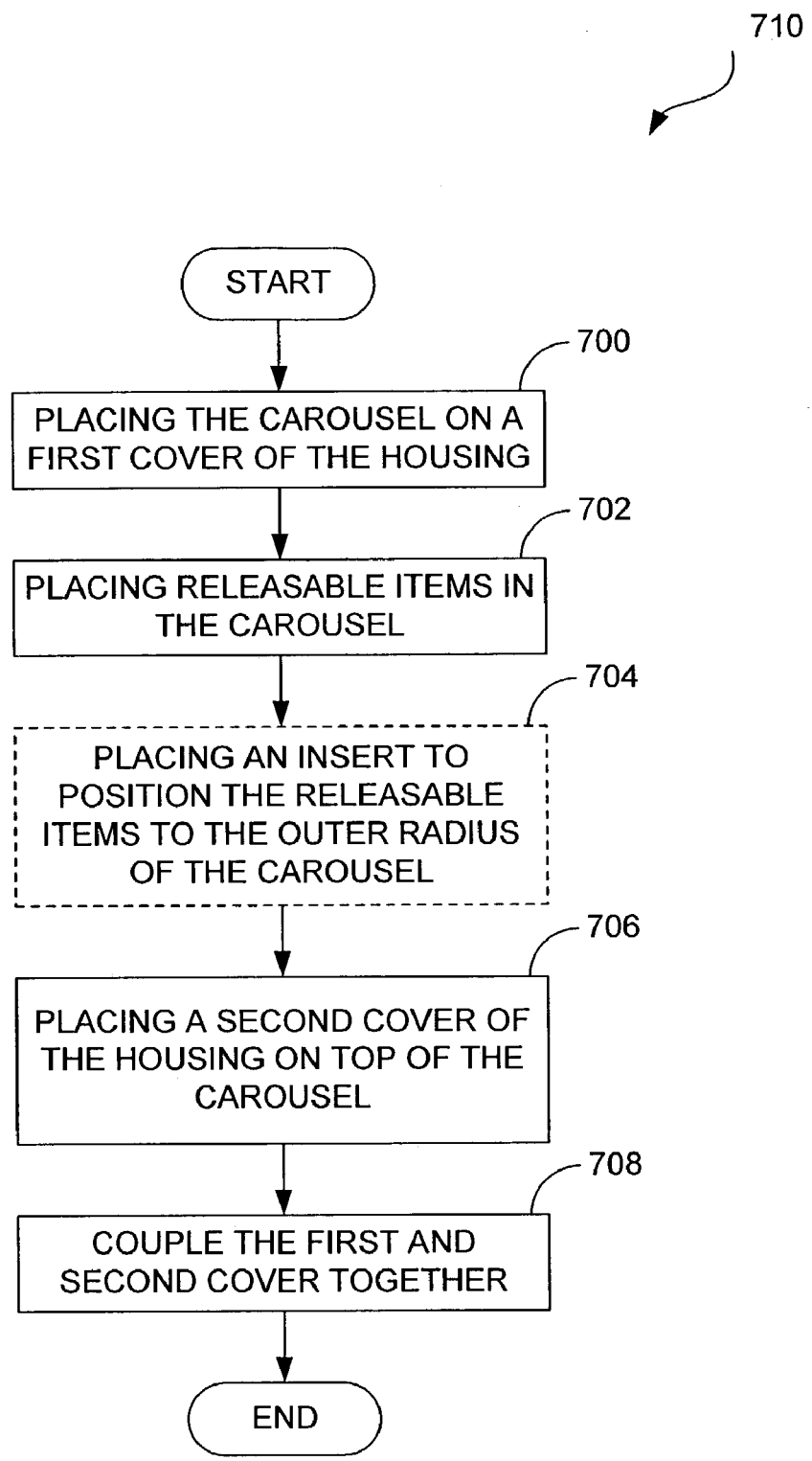
FIG. 7 is a flow diagram that illustrates an example of a method of assembling the cartridge that facilitates releasing releasable items.

FIG. 7 illustrates an example of a method 710 of assembling the cartridge 200, 201 with partitioning insert 302 that facilitates releasing releasable items, i.e., pills, capsules, tablets, medications, and drugs. Beginning with block 700 of FIG. 7, the carousel is placed on a first cover of the case of the cartridge 200, 201. The first cover may include a reprogrammable readable memory 308, as shown in FIG. 3, on a PCB board. The first cover of the case may include an opening 360 (shown in FIG. 3) such that the releasable items may be released through the opening of the cartridge. In block 702, the releasable items, i.e., pills, capsules, tablets, medications, and drugs, are placed in the carousel. In block 704, the partitioning insert 302 may be placed in the carousel 304 to position the releasable items towards the outer radius of the carousel. In block 706 of FIG. 7, a second cover of the case of the cartridge is placed on top of the carousel and coupled to the first cover to form the cartridge. In block 708, the first and second covers of the case are coupled together to form cartridge 200, 201. The second cover of the case has an opening 360 such that the releasable items may be released through the opening 360 of the cartridge 200, 201.

Figure 17:
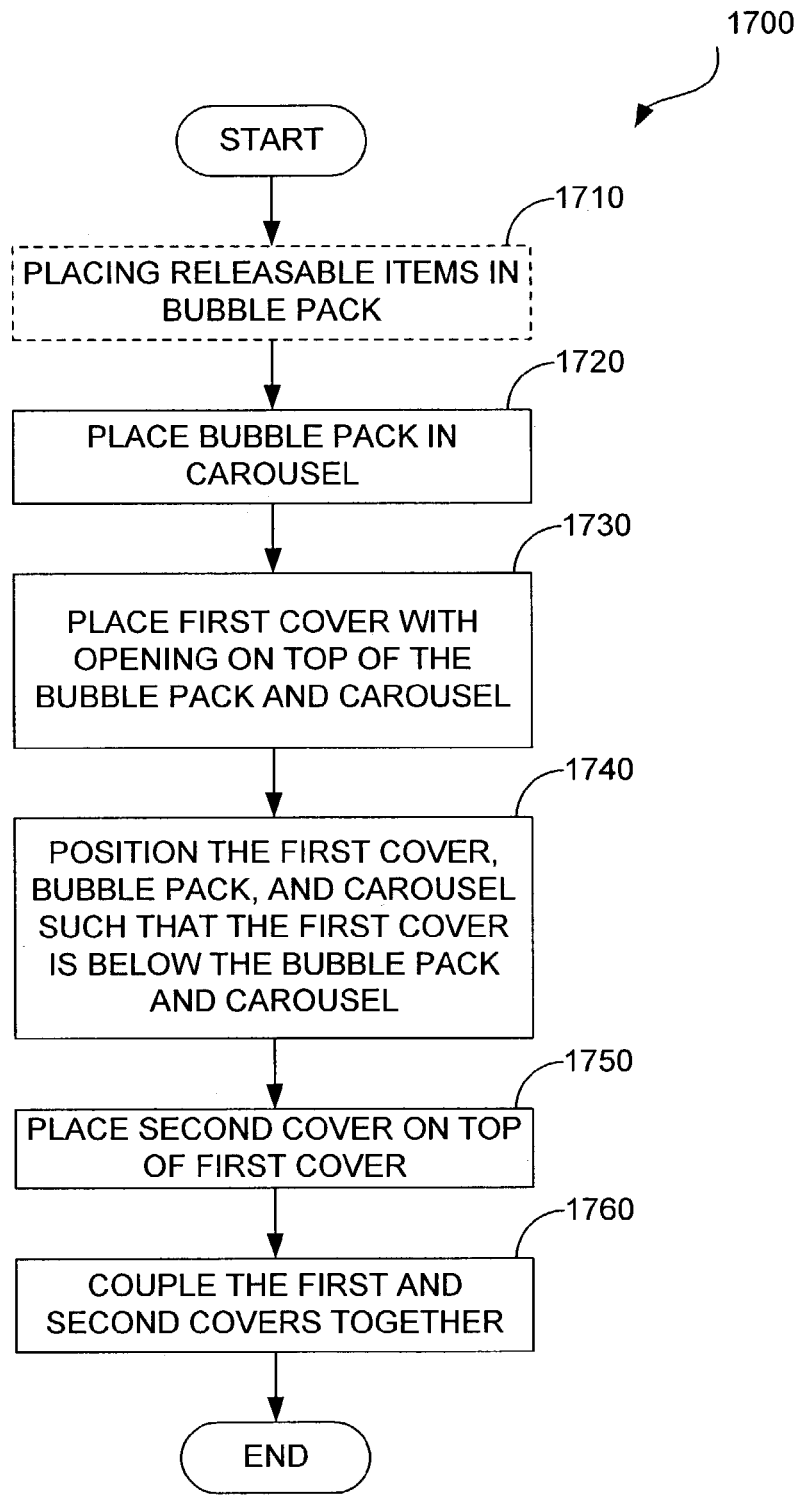
FIG. 17 is a flow diagram that illustrates an example of a method of assembling the cartridge with a bubble pack.

FIG. 17 provides an example of a method 1700 of assembling the cartridge 200, 201 with the bubble pack 600. The bubble pack 600 may be filled with releasable items. The bubble pack may include the aligning space 618 that contains no releasable item and allows the assembler to align the aligning space 618 with the opening of the cartridge. In block 1720, the bubble pack 600 is placed in carousel 304.

In block 1730 of FIG. 17, a first cover of the case of the cartridge is placed on top of the bubble pack 600 and carousel 304. The first cover may include an opening 360 through which the releasable items, i.e., pills, capsules, tablets, medications, and drugs, are released from the cartridge. In block 1740, the first cover, bubble pack and carousel are positioned in such a way that the first cover is below the bubble pack 600 and the carousel 304. The bubble pack is now positioned such that the releasable items, i.e., pills, capsules, tablets, medications, and drugs, can fall out of the opening 614 of the sack 602 of the bubble pack 600 and through the opening 360 of the first cover of the cartridge 200, 201. In block 1750, the second cover is placed on top of the carousel and in block 1760, the first and second cover are coupled together to form cartridge 200, 201.

FIG. 8 is a block diagram illustrating an example architecture for the releasing units 102, 104, 106, 118, 126 shown in FIG. 1. As indicated in FIG. 8, the releasing units 102, 104, 106, 118, 126 comprise a processing device 800, memory 802, one or more user interface devices 804, one or more I/O devices 806, and one or more networking devices 808, each of which is connected to a local interface 810. The processing device 800 can include any custom made or commercial available processor, a central processing unit (CPU) or an auxiliary processor among several processors associated with the releasing units, a semiconductor-base microprocessor (in the form of a microchip), or a microprocessor. The memory 802 can include any one or a combination of volatile memory elements (e.g., random access memory (ram, such as DRAM, SRAM, etc.) and non volatile memory elements (e.g., ROM, hard drive, tape, CDROM, etc.)).

The one or more user interface devices 804 comprise those components with which the user (e.g., patient, caretaker, etc.) can interact with the releasing unit 102, 104, 106, 118, 126. By way of example, the user interface devices 804 comprise one or more function keys and/or buttons (206, 208 as shown in FIG. 2) with which the operation of the releasing unit 102, 104, 106, 118, 126 can be controlled, and a display (204 as shown in FIG. 2), such as a liquid crystal display (LCD), with which information can visibly communicated to the user which commands may be entered by the user. The one or more I/O devices 806 comprise components used to facilitate connection of the releasing unit 102, 104, 106, 118, 126 to other devices, such as the cartridge 200, 201, and therefore, for instance, comprise one or more serial, parallel, small system interface (SCSI), universal serial bus (USB), or IEEE 1394 (e.g., FireWire™) connection elements, i.e., interface device 512 as shown in FIG. 5. In addition, the releasing unit 102, 104, 106, 118, 126 further includes a releasing engine 816 that can comprise, for instance, a motor 504, sensing arm 508, unlocking arm 502, and cartridge locking arm 510, shown in FIG. 5.

The networking devices 808 comprise the various components used to transmit and/or receive data over the network 130 and/or telephone line, and/or the network 130 using user-computing devices where provided. For instance, as shown in FIG. 1, releasing units 102, 104, 106 have networking devices that communicate over the telephone line. Releasing units 118, 126 have devices that communicate to user-computing device 116, 124, which, in turn, over the network 130. Releasing unit 122 is further described in relation to FIG. 9. By way of example, the network devices 808 include devices that can communicate both inputs and outputs, for instance, a modular/demodular (e.g., modem), a radio frequency (RF) or infrared (IR) transceiver, a telephonic interface, a bridge, a router, as well as a network card, etc.

The memory 202 normally comprises various programs (in software and/or firmware) including an operating system (O/S) 812 and a releasing unit manager 814. The operating system 812 controls the execution of programs, including the releasing unit manager 814, and provides scheduling, input-output control, file and database management, memory management, and communication control and related services. The releasing unit manager 814 facilitates the process for releasing releasable items, i.e., pills, capsules, tablets, medications, and drugs, from the releasing unit 102, 104, 106, 118, 126. Typically, the process involves receiving information corresponding to the items from the cartridge 200, 201 and releasing the releasable items in accordance with the received information. The process also includes gathering data of the activities of the releasable items and sending the data to a central-computing device. The process may further include programming the activities data into the cartridge. The process facilitates the releasing of the items, i.e., pills, capsules, tablets, medications, and drugs. Operation of the releasing unit manager 814 is described in relation to FIGS. 13 and 14.

Figure 9:
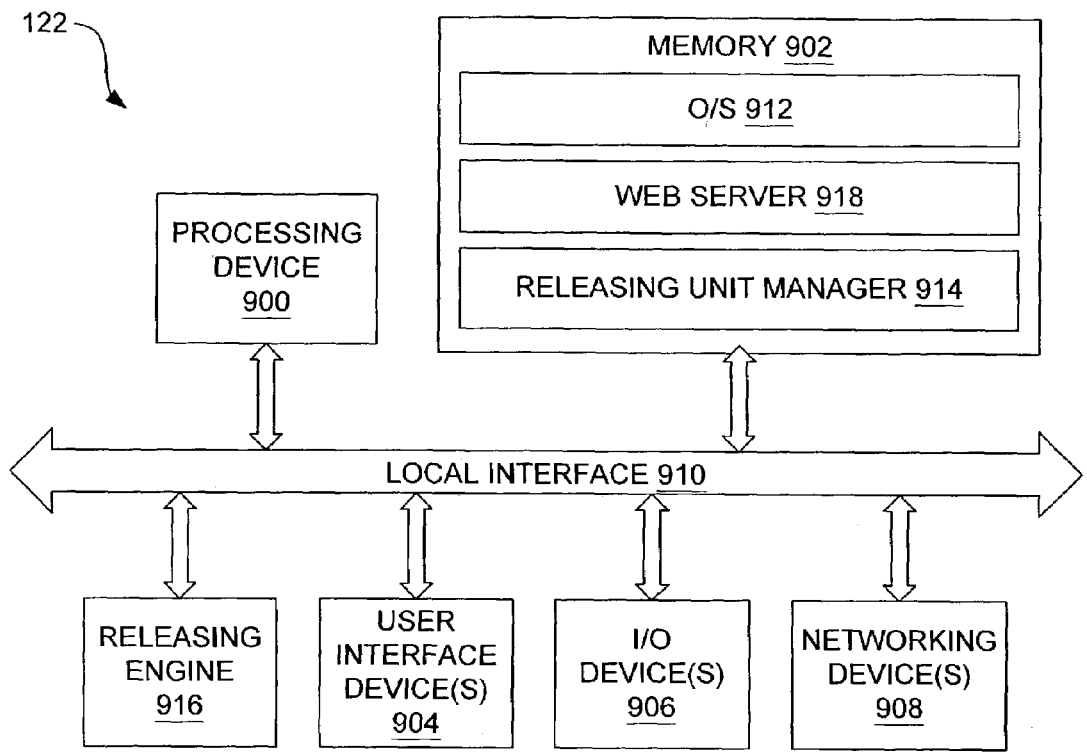
FIG. 9 is a block diagram illustrating an example architecture of a releasing unit shown in FIG. 1 that can communicate with the central-computing device via the network without communicating to a user-computing device.

FIG. 9 is a block diagram illustrating an example architecture of a releasing unit 122 shown in FIG. 1 that can communicate with the central-computing device 108 via the network 130 without communicating to a user-computing device 116, 124. The architecture of the releasing unit 122 is similar to the architecture of the releasing units 102, 104, 106, 118, 126 and therefore includes a processing device 900, memory 902, 1/0 devices 902, networking devices 908, and releasing engine 916, each of which has a configuration similar to those described above, and each being connected to a local interface 910.

The memory 902 includes various programs (in software and/or firmware) including an O/S 912 that contains the various commands used to control the general operation of the releasing unit 122 and optionally, an embedded web server 918. In addition, the memory 902 includes a releasing unit manger 914 that facilitates releasing releasable items to a user. The process for the releasing unit manager 914 is similar to the process of the releasing unit manager 814 and such operation or process is further described in relation to FIGS. 13 and 14.

Figure 10:
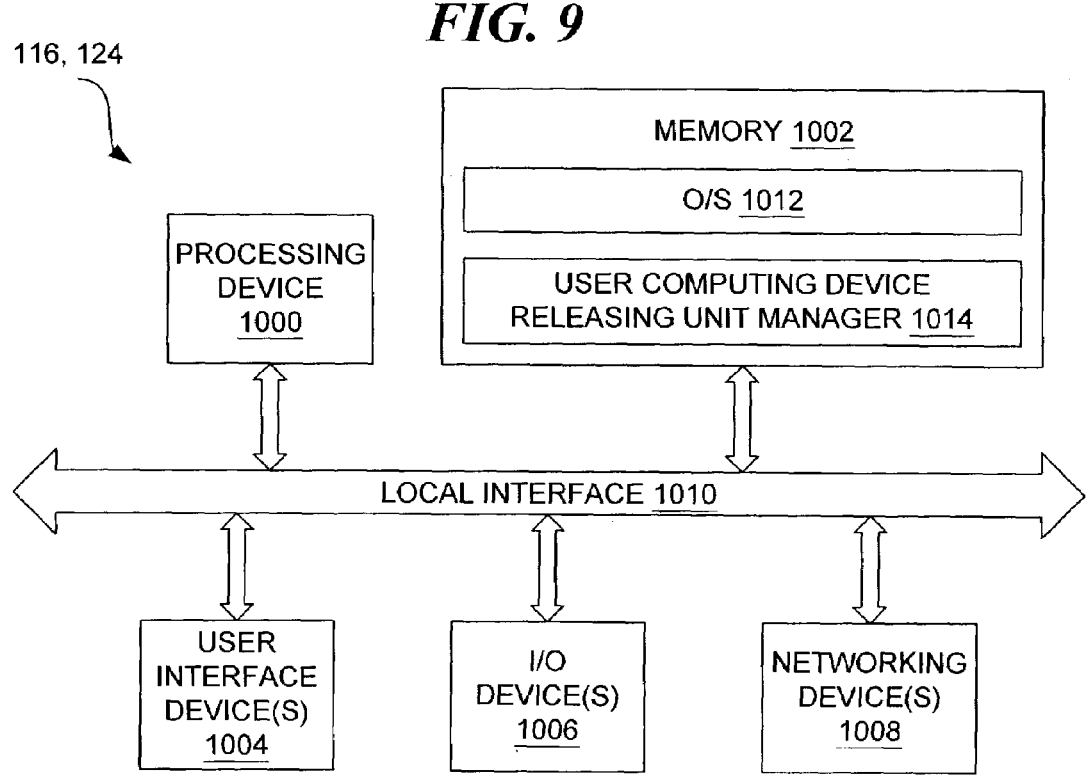
FIG. 10 is a block diagram illustrating an example architecture for the user-computing device shown in FIG. 1.

FIG. 10 is a block diagram illustrating an example architecture for the user-computing devices 116, 124 shown in FIG. 1. The architecture for the computing device 116, 124 is similar to the architecture of the releasing units described above and therefore includes a processing device 1000, one or more user interface devices 1004, one or more I/O devices 1006, and one or more networking devices 1008, each of which is connected to a local interface 1010. The memory 1002 in the user-computing device 116, 124, however, includes a user-computing device releasing unit manager 1014 that facilitates releasing releasable items to a user. Typically, the user-computing device releasing unit manager 1014 gathers data corresponding to the releasable items and the releasing activities of releasable items from the releasing unit. The data is then sent to the central server 108.

Figure 11:
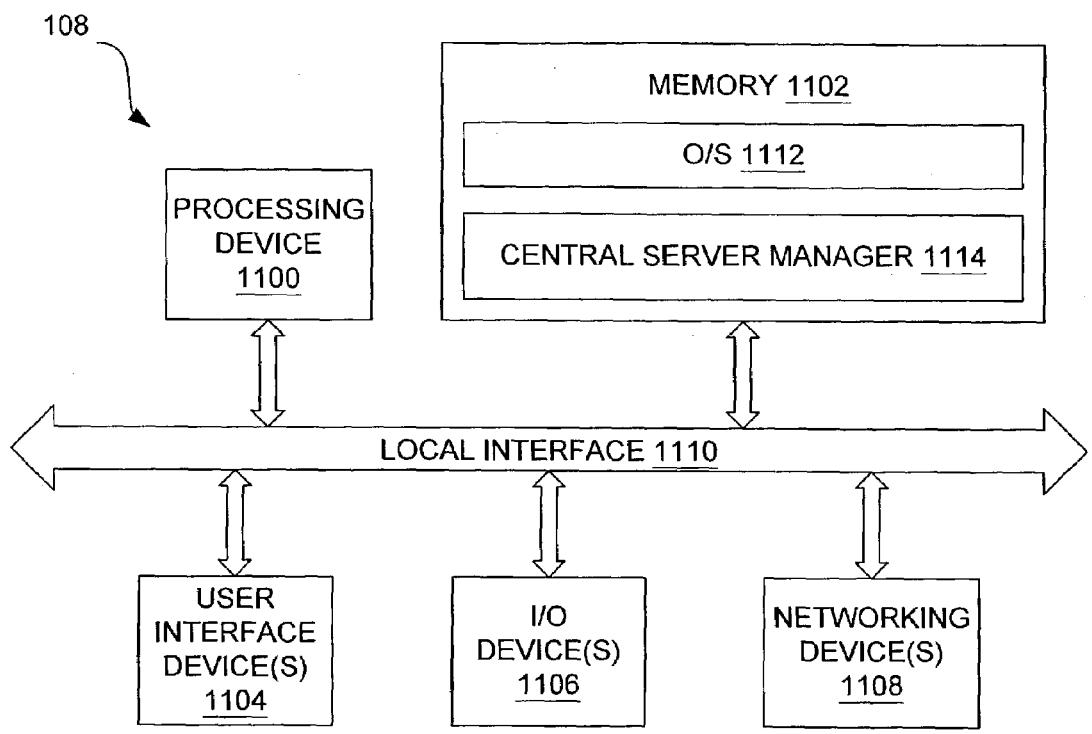
FIG. 11 is a block diagram illustrating an example architecture for the central-computing device shown in FIG. 1.

FIG. 11 is a block diagram illustrating an example architecture for the central-computing device 108 shown in FIG. 1. The architecture for the central-computing device 108 is similar to the architecture of the user-computing devices 116, 124 described above and therefore includes a processing device 1100, one or more user interface devices 1104, one or more I/O devices 1106 and one or more networking devices 108, each of which is connected to a local interface 1110.

The memory 1102 in the central server 108, however, includes a central server manager 1114 that facilitates dispensing the releasable item from a provider. Typically, the central server manager 1114 gathers data corresponding to the releasable items and the activities related to the releasable items via the network 108 and/or telephone line. The manager 1114 further communicates the data to the provider-computing devices 110, 112, 114, 128, 120. Operation of the central server manager 114 is described in relation to FIGS. 13 and 15.

Figure 12:
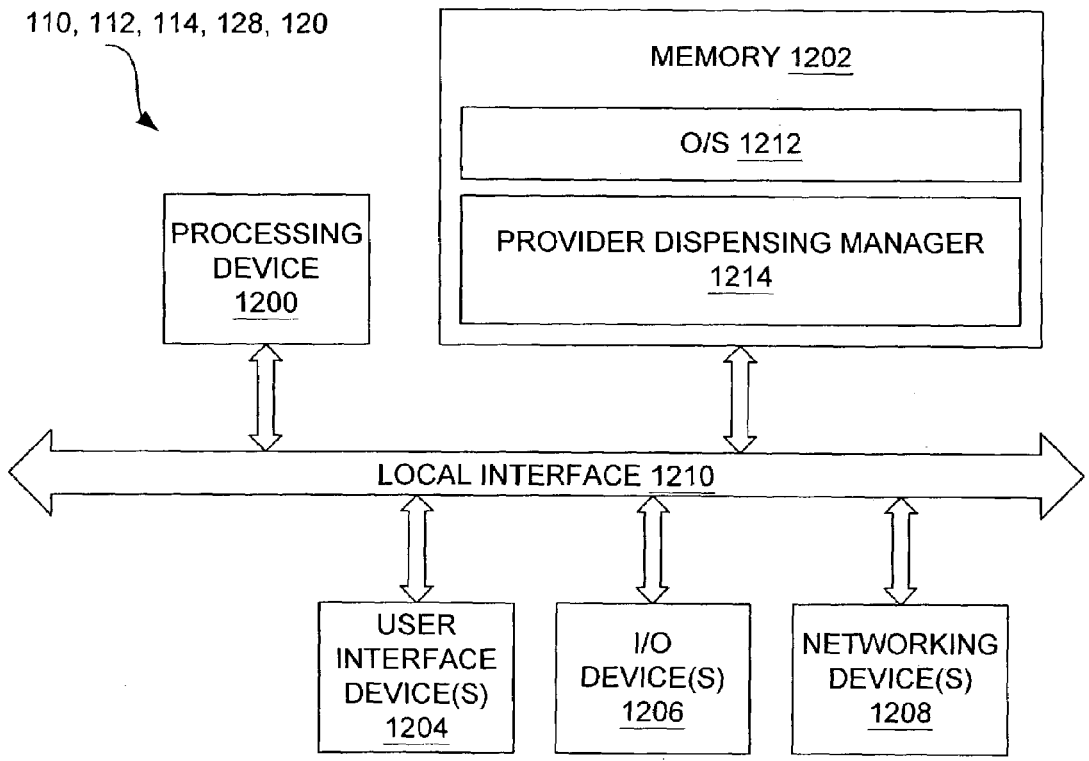
FIG. 12 is a block diagram illustrating an example architecture for the provider-computing device shown in FIG. 1.

FIG. 12 is a block diagram illustrating an example architecture for the provider-computing devices 110, 112, 114, 120, and 128 shown in FIG. 1. The architecture for the provider-computing devices 110, 112, 114, 120, 128 is similar to the architecture of the central-computing device 108 described above and therefore includes a processing device 1200, one or more user interface devices 1204, one or more I/O devices 1206, and one or more networking devices 1208, each of which is connected to a local interface 1210.

The memory 1202 in the provider-computing devices 110, 112, 114, 120, and 128, however, include a provider dispensing manager 1214 that facilitates dispensing releasable item to a user. Typically, the provider dispensing manager 1214 receives data corresponding to the releasable items and activities in relation to the releasable items via the network 130 and/or telephone line. The manager 1214 further displays the information to the provider, i.e., pharmacist. The provider can then decide whether to obtain the releasable items to the user from the provider's facility. In which case, the provider programs the cartridge containing the releasable items to include information on the releasable items. Operation of the provider dispensing manager 1214 is further described in relation to FIGS. 13 and 16.

Various programs have been described above. It should be understood that these programs could be stored on any computer-readable medium for use by or in connection with any computer-related system or method. In the context of this document, a computer-readable medium is an electronic, magnetic, optical, or other physical device or means that can contain or store a computer program for use by or in connection with a computer-related system or method. The programs can be embodied in any computer-readable medium for use by or in connection with an instruction execution system, apparatus, or device, such as a computer-base system, processor-containing system or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device.

The computer-readable medium can be, for example, an electronic, magnetic, optical, electromagnetic, infrared, or semiconductors system, apparatus, device, or propagation medium. More specific examples (a nonexhaustive list) of the computer-readable medium include an electrical connection having one or more wires, a portable computer diskette, a random access memory (RAM), a read-only memory (ROM), and an erasable programmable read-only memory (EPROM, EEPROM, or flash memory), an optical fiber, and a portable compact disk read-only memory (CDROM). Note that the computer-readable medium can even be paper or another suitable medium upon which a program is printed, as the program can be electronically captured, via for instance optical scanning of the paper or other medium, then complies, interpreted or otherwise process in a suitable manner if necessary, and then stored in a computer memory.

Example systems having been described above, system operation will now be discussed. In the discussions that follow, flow diagrams are provided. Any process steps or blocks in these flow diagrams may represent modules, segments, or portions of code that include one or more executable instructions for implementing specific logical functions or steps in the process. Although particular example process steps are described, alternative implementations are feasible. Moreover, steps may be executed out of order from that shown or discussed, including substantially, concurrently or in reverse order, depending on the functionality involved.

Figure 13:
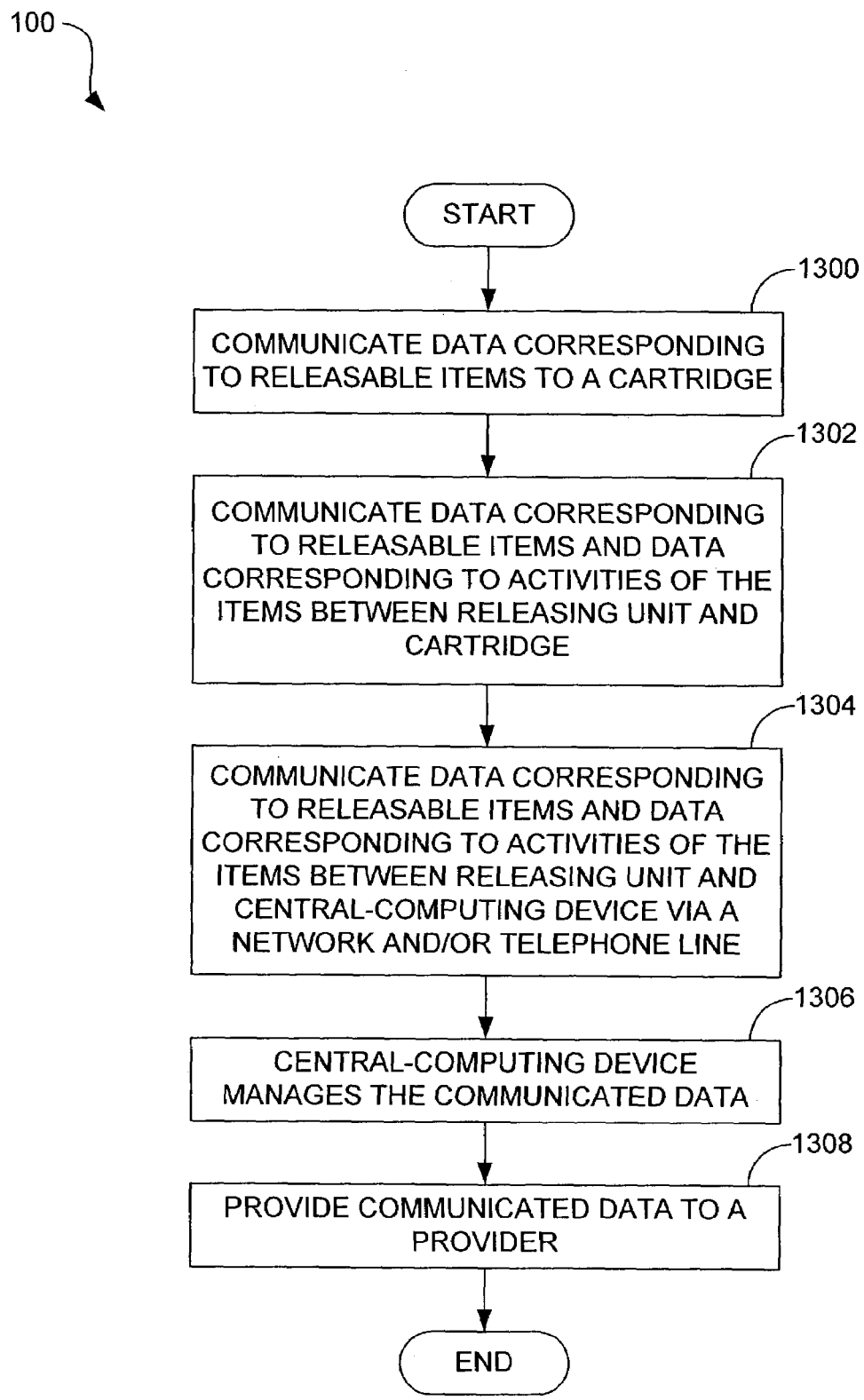
FIG. 13 is a flow diagram that illustrates an embodiment of operation of the system shown in FIG. 1 in processing the releasing and/or dispensing of the releasable items.

FIG. 13 illustrates a high-level example of operation of the system 100 in processing the releasing and dispensing of the releasable items. With the system 100, a user may automatically and properly obtain releasable items, such as pills, capsules, tablets, medications, and drugs. For example, a user may obtain pills, capsules, tablets, medications, and drugs from the releasing units on a daily basis at the proper time. The releasing units may also release the medication every other day, weekly, or biweekly, depending on when the pharmacist would like the medication to be administered to the patient. A user may also obtain a refill of the pills, capsules, tablets, medications, and drugs from a provider, such as a pharmacist, in a timely fashion.

It should be noted that the "releasing" and "dispensing" differs in the fact that a provider, such as pharmacist, dispenses pills, capsules, tablets, medications, and drugs to a patient. The provider prepares the pills, capsules, tablets, medications, and drugs in the cartridge to dispense to the patient. On the other hand, the patient places the cartridge in the releasing unit for releasing the pills, capsules, tablets, medications, and drugs. Pharmacists are the only persons legally allowed to dispense pills, capsules, tablets, medications, and drugs to a patient. In this regard, the releasing unit releases pills, capsules, tablets, medications, and drugs to the patient.

Beginning with block 1300, the system 100 for processing the releasing and dispensing of releasable items communicates data corresponding to releasable items, such as pills, capsules, tablets, medications, and drugs, to a cartridge 200, 201. The data may, for example, comprise the name of the medication, the amount of dosage for each medication, the name of the doctor that prescribed the medication, the quantity of medication taken, the time to take the medication, side effect of the medication, the makeup of the medication, expiration date, number of refills, patient's name, facility's name, patient's identification, prescription number, etc. In short, the data comprises information that the pharmacist may provide to the patient when dispensing the medication.

In block 1302, the system 100 communicates data corresponding to the releasable items and activities related to the items between the releasing unit and the cartridge. The activities of the item may, for example, comprise when the releasable items were released to a user, how many releasable items were released, how many releasable items were not released, who released the items, etc.

In block 1304, the system 100 communicates the data corresponding to the releasable item and activities related to the items between the releasing units 102, 104, 106, 118, 122, 126 and central-computing device 108 via a network 130 and/or telephone line. In block 1306, the central-computing device 108 manages the communicated data. In block 1308, the central-computing 108 provides the communicated data to a provider.

Figure 14:
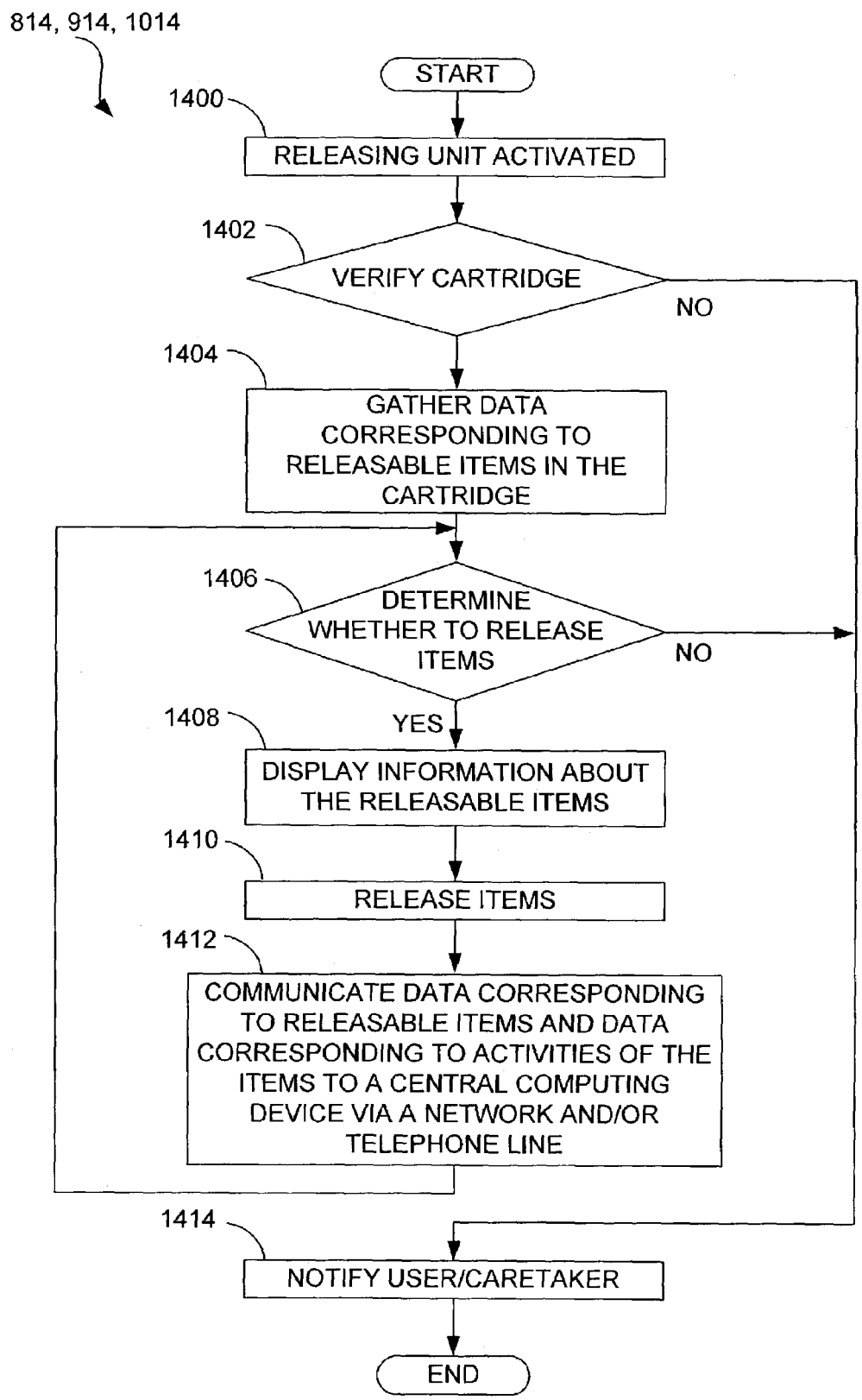
FIG. 14 is a flow diagram that illustrates an embodiment of operation of a releasing unit manager that facilitates releasing and/or dispensing of releasable items.

FIG. 14 illustrates an example of operation of a releasing unit manager 814, 914 that facilitates releasing and dispensing of releasable items, such as pills, capsules, tablets, medications, and drugs. This manager can comprise the releasing unit manager 814 of the releasing unit 102, 104, 106, 118, 126, or the manager 914 of the releasing unit 122 that contains an embedded web server 918 as shown in FIG. 9. The releasing unit manager is activated, as indicated in block 1400, when the releasing unit is powered up. The releasing unit then waits for the insertion of a cartridge 200, 201. When the cartridge 200, 202 is inserted into the releasing unit, the manager 814, 914 verifies whether the cartridge is authorized for usage with the releasing unit, as shown in block 1402. For instance, the cartridge may be preprogrammed with a releasing unit identification in the memory of the electronic chip 308 of the cartridge. When the releasing unit verifies the cartridge, it determines whether the releasing unit identification stored in the electronic chip 308 of the cartridge is the same with the releasing unit identification stored in the memory in the releasing unit. If the identification data stored in the releasing unit and the cartridge is not a match, then the releasing unit notifies the user and/or caretaker that the cartridge is not authorized for usage with the releasing unit, as shown in block 1414. The notification may be beeped on a speaker, displayed on the LCD display 204 and/or indicated with flashing lights 238, as shown in FIG. 2. The notification may also include paging a caretaker and/or user via a modem to replace the non-matching cartridge with a matching cartridge. The paging may be directed to at least one person. If the first paged person does not respond, then it pages a second person, and so on.

If the manager 814, 914 verifies that the cartridge 200, 201 was authorized for usage with the releasing unit, the releasing unit gathers data corresponding to the releasable items, i.e., pills, capsules, tablets, medications, and drugs, in the cartridge, as shown in block 1404. For example, the data may be gathered from the memory of the electronic chip 308.

As shown in block 1406, releasing unit determines whether to release the releasable item, in accordance with the gathered data in the cartridge. The releasing unit manager 814, 914 determines the time and amount of releasable items that the releasing unit releases to a user. The releasing unit manager 814, 914 may include an internal real-time clock, which the manager 814, 914 uses to monitor when to release the releasable items. If the releasable items, such as pills, capsules, tablets, medications, and drugs, are not released within a predetermined time, then the manager 814, 914 notifies the user/caretaker as indicated in block 1414. As stated above, the notification may be displayed, indicated with flashing lights, beeped with a speaker, and/or paged to a user/caretaker. If the releasable items are released within the predetermined time, then the manager 814, 914 displays information about the releasable items, as indicated in block 1408. The information may contain, but not limited to, the ingredients or make up of the releasable items, instructions for ingesting the releasable items (in the case of pills, capsules, tablets, medications, and drugs), what to do before ingesting the pills, capsules, tablets, medications, and drugs, etc.

In block 1410, the manager 814, 914 releases the releasable items. If multiple cartridges need to be released at the same time period, the manager 814, 914 may be programmed to release the items in the cartridges all at once or separately. The user may need to acknowledge the manager 814, 914, such as pressing a release button 208, as shown in FIG. 2, to indicate that the user is present to take the releasable item from the releasing unit. The releasing unit releases the items by rotating the carousel 304 in the cartridge such that the items in the carousel 304 are released through the discharge opening 360 of the cartridge. The user may also need to pull the drawer 202 out of the releasing unit to access the items from the releasing unit. By pressing the button and/or pulling the drawer, the manager 814, 914 records and updates in memory the time and quantity of items that were released from the cartridge and taken from the drawer.

Once the releasable item is released to the user, the manager 814, 914 maintains a database of the activities of the releasable items, such as when and how many releasable items are released to a user. In block 1412, the manager 814, 914 communicates the data corresponding to the releasable items and activities of the items to the central-computing device 108 via the network 130 and/or telephone line. In the case of transmitting the data via a network, a user-computing device 116, 124 may be provided to relay the information from the releasing unit 118, 126 to the network 130 such that the central-computing device 108 may receive the information from the releasing unit. Alternatively, the releasing unit may relay the information to a network directly by way of an embedded web server 918 of the releasing unit 122.

In the case of communicating data over a telephone line, the releasing units 102, 104, 106 may include a modem to transmit the data corresponding to releasable items and activities related to the items to the central-computing device 108. Once the data is communicated to the central-computing device 108, the manager 814, 914 continues back to block 1404 to determine whether to release the releasable item.

It should be noted that the manager 814, 914 may also operate with non-releasable items, such as eye drops. The manager 814, 914 may also remind the user/caretaker to, for instance, measure blood pressure and blood sugar levels. An empty cartridge may be programmed with data corresponding to the non-releasable item. For example, the data includes the time and quantity of non-releasable items should be administered, reminders when to notify the user, patient ID number, releasing unit ID number, etc. The manager 814, 914 operates similarly with non-releasable items as described above with reference to FIG. 14 to remind the user/caretaker accordingly.

Figure 14A:
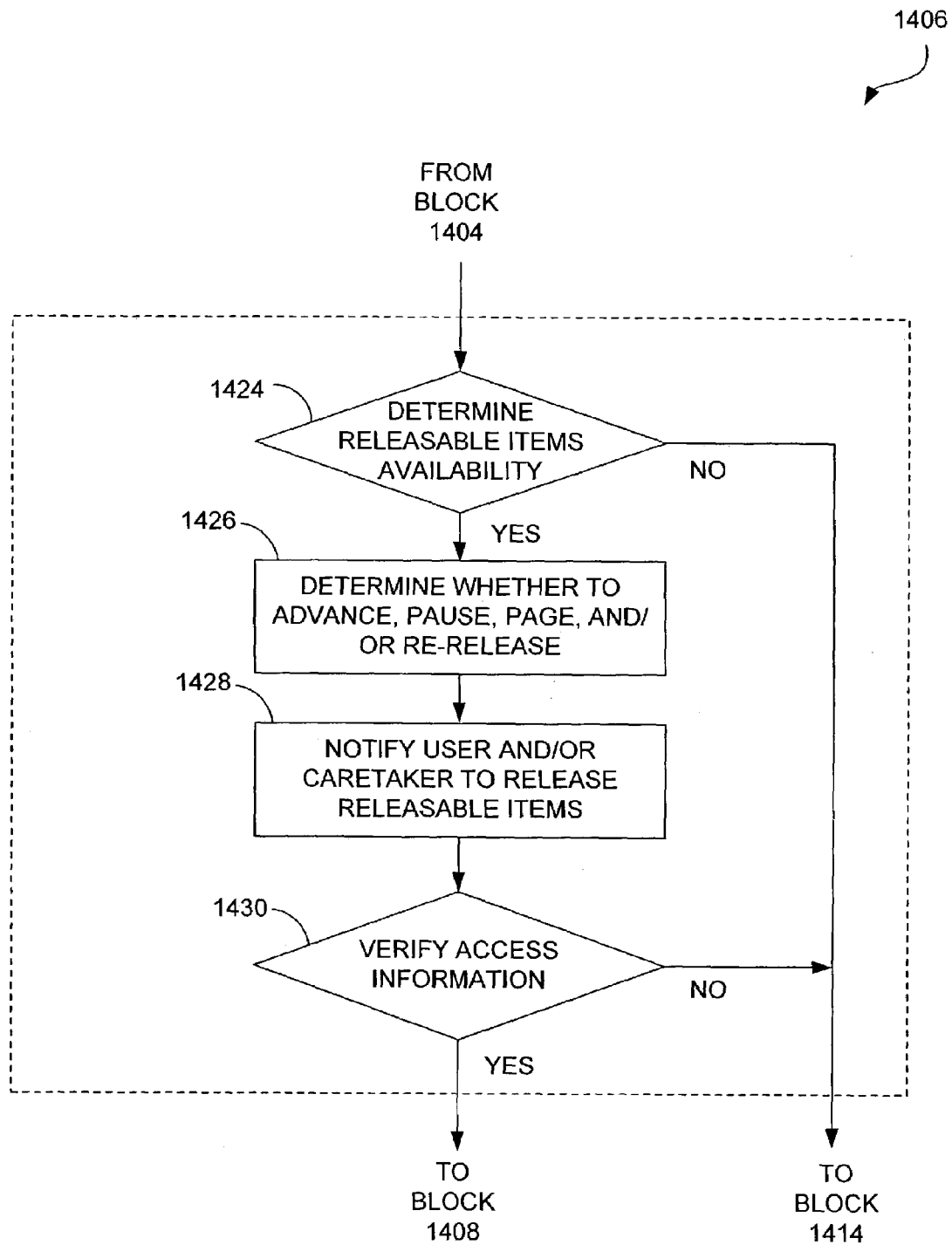
FIG. 14A is a flow diagram that illustrates an example of operation of block 1404 of FIG. 14.

FIG. 14A illustrates an example of operation of block 1406 of FIG. 14 in which the releasing unit manager 814, 914 determines whether to release the releasable items. In addition to determining the time and quantity of releasable items to release to the user, the manager 814, 914 further determines whether the releasable items are available in the cartridge 200, 201, as indicated in block 1424. If the releasable items are not available in the cartridge, the manager 814, 914 notifies the user/caretaker that the releasable items are no longer available to be released to a user by displaying the information, flashing lights, paging the user/caretaker, and/or beeping a noise. In addition, the data corresponding to the availability of the releasable item is communicated to the central-computing device, as indicated in block 1412 of FIG. 14.

If the manager 814, 914 determines that the releasable items are available in the cartridge to be released to a user, the manager 814, 914 then determines whether the user has opted to advance the releasable items, pause the activities of the releasing unit and/or re-release the releasable items due to error in initially releasing the releasable items, as indicated in block 1426. The user selects the features indicated above via the user interface of the releasing unit as shown in FIG. 2. The manager 814, 914 further determines whether to page the user/caretaker via a modem. In the case of advancing the releasable items, the user may need a number of releasable items, such as pills, capsules, tablets, medications, and drugs, in case the user is away from the releasing unit for an extended period of time, such as four days or during a vacation. In the case of pausing the releasing unit, the user may be unable to use the releasing unit due to a necessary stay in a hospital or other healthcare facility. The releasing unit may be paused from operating its normal activities until the user is back from the hospital or other healthcare facility. In the case of paging the user/caretaker, the manager 814, 914 may determine that the releasable items should be released at a predetermined time and therefore pages the user/caretaker to release the releasable items, such as pills, capsules, tablets, medications, and drugs. In the case of re-releasing the releasable items, the manager 814, 914 may determine that the initial release of the releasable item, i.e., pills, capsules, tablets, medications, and drugs, was damaged or unstable for the user and re-release the item to the user.

In block 1428, the manager 814, 914 notifies the user/caretaker to release the releasable items either by way of displaying the notification on a LCD display, beeping on a speaker, paging the user/caretaker, and/or flashing lights on the releasing unit. In block 1430, the manager 814, 914 may verify the access information provided by the user. The access information may include, for example, a social security number, the name of the user, the user's facility provided number, or any other information that may be used to verify the user and/or the user's verification to release the releasable items. The user enters the access information (or pass code) into the releasing unit by way of the user interface devices (i.e., buttons 206, display 204, light components 238, etc.). If the manager 814, 914 cannot verify the access information provided by the user, the manager 814, 914 continues to block 1414, which notifies the user/caretaker that an invalid access information was provided to the releasing unit. This activity is recorded in the memory of the releasing and transmitted to the central-computing device 108 via the network 130 and/or telephone line. If the manager 814, 914 verified that the access information is valid, then the manager 814, 914 continues to block 1408, which displays the information about the releasable items.

Figure 15:
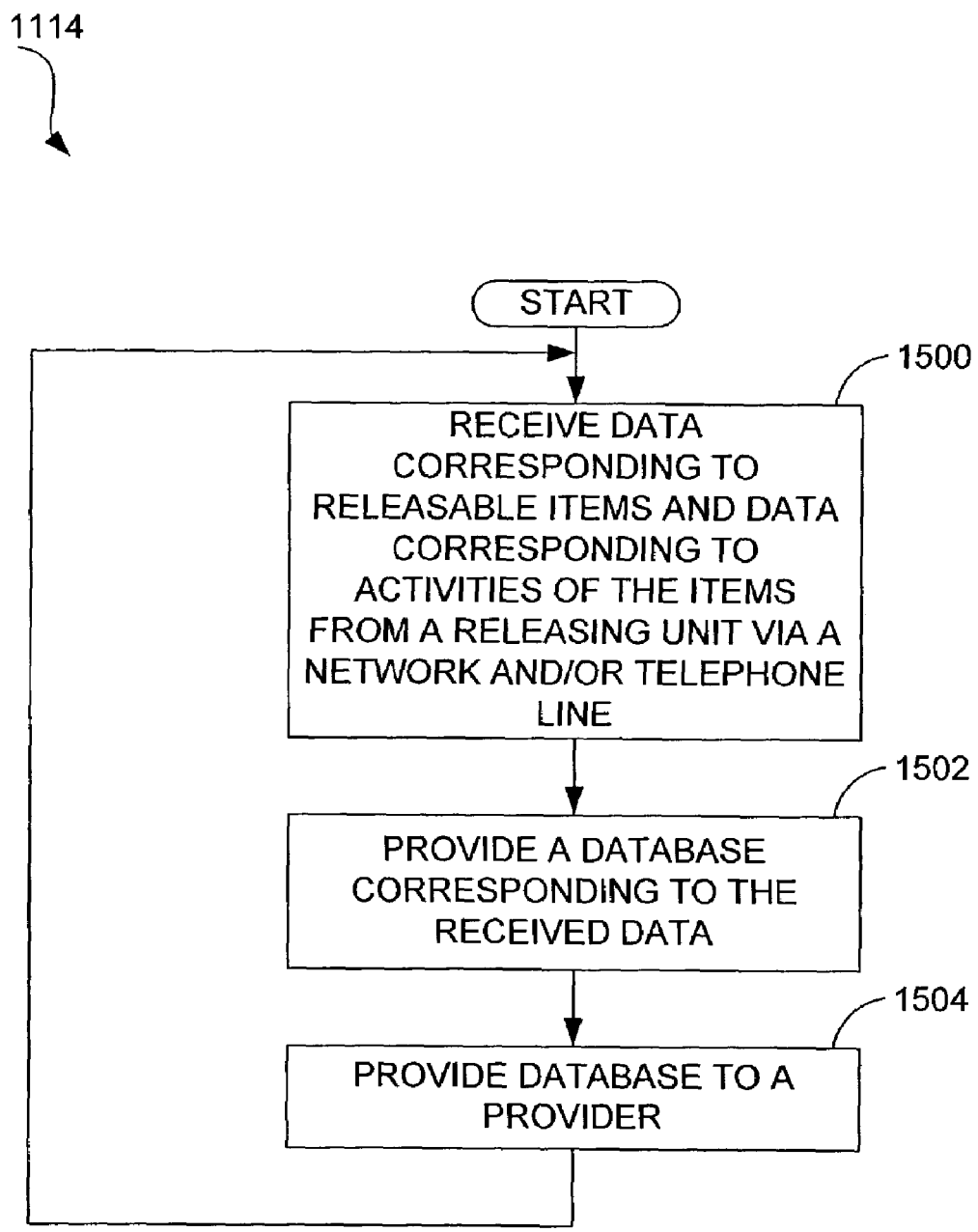
FIG. 15 is a flow diagram that illustrates an embodiment of operation of a central server manager that facilitates dispensing releasable items.

FIG. 15 illustrates an example of operation of a central server manager 1114 that facilitates dispensing the releasable items. Beginning with block 1500 of FIG. 15, the central server manager 1114 communicates data corresponding to the releasable items and the activities of the items from the releasing unit via the network 130 and/or telephone line. The manager 1114 provides a database corresponding to the communicated data as shown in block 1502. The database may include the amount of dosage per releasable item, the name of the releasable item, the manufacture of the releasable item, the doctor that prescribed the releasable item, the time and amount that the releasable item were released from the releasing unit, etc. In block 1504, the central server manager 1114 provides the database to a provider, i.e., pharmacist. The manager 1114 may communicate the database to a provider-computing device 110, 112, 114 via a telephone line and/or a provider-computing device 120, 128 via a network 130. The provider may obtain the database from the provider-computing device and determine whether the user properly released the releasable items from the releasing unit and determine whether to provide a new supply of the releasable items in the cartridge and to dispense the cartridge to the user. The manager 1114 continues to receive data from the releasing unit and updates the database.

Figure 16:
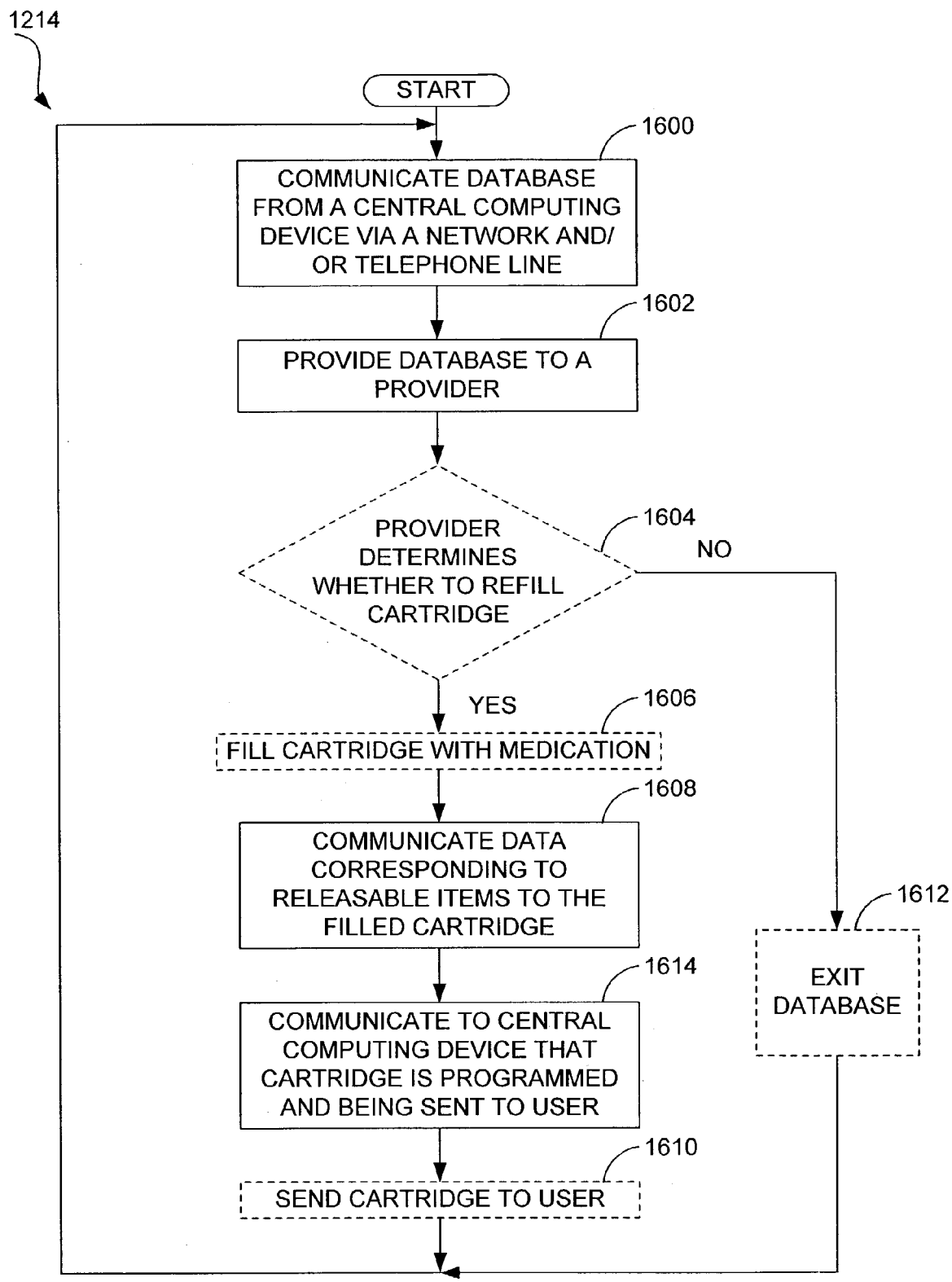
FIG. 16 is a flow diagram that illustrates an embodiment of operation of a provider dispensing manager that facilitates dispensing of the releasable items.

FIG. 16 illustrates an example of operation of the provider dispensing manager 1214 that facilitates dispensing of the releasable items. Beginning with block 1600 of FIG. 16, the provider dispensing manager 1214 receives the database from the central-computing device 108 via a network 130 and/or telephone line. When the database is needed, the provider, i.e., pharmacist, obtains the database from the provider-computing device, as indicated in block 1602. In block 1604 of FIG. 16, the provider determined whether to provide a new supply of the releasable items in the cartridge in accordance with the database received from the central-computing device 108. This allows the provider to provide a new supply of the releasable items in the cartridge based upon perpetual real time data received from the central-computing device 108.

If the provider determined that there is no need to provide a new supply in the cartridge, the provider exits out of the database of the provider-computing devices, as indicated in block 1613, and the manager 1214 continues to communicate and update the database from the central-computing device 108. If the provider determines that a new supply is needed, then the provider fills the cartridge with medication as indicated in 1606. The provider communicates data corresponding to filled cartridge, as shown in block 1608. The manager 1214 communicates to the central-computing device 108 via the network 130 and/or telephone line that cartridge is programmed and being sent to the user. The provider sends the filled cartridge to the user (as shown in 1610). The manager 1214 continues to communicate and update the database from the central server 108 via the network 138 and/or telephone line. The data communicated to the cartridge may be transmitted to a cartridge programming unit, which may be a reprogrammed releasing unit that communicates with the provider-computing device and programs the filled cartridge with data corresponding to the releasable items.

It should be noted that blocks 1604, 1606, 1610 were explained in the context that a provider, i.e., pharmacist, carried out the steps. However, these steps may be automated such that the manager 1214 determines whether to refill the cartridge. A cartridge refilling device in communication with the manager 1214 fills the cartridge, and a packaging and shipping device in communication with the manager 1214 packages and prepares the filled cartridge for shipping to the user.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included here in within the scope of this disclosure and the present invention and protected by the following claims.

Therefore, having thus described the invention, at least the following is claimed:

1. A releasing apparatus for releasing releasable items in sequence, said apparatus comprising:
   a housing defining a plurality of cartridge slots;
   at least one cartridge for insertion into at least one of said cartridge slots, each of said cartridges including a case and a carousel rotatably received in said case about a central axis of rotation;
   said carousel comprising multiple compartments arranged in a circular array about the central axis of rotation of said carousel for storing the releasable items, each compartment having a release opening;
   said case defining a discharge opening in alignment with said circular array of compartments for registering with said release openings of each of said compartments in sequence as said carousel rotates; and
   a bubble pack being comprised of multiple sacks, which are placed in said multiple compartments arranged in said circular array about said central axis of rotation of said carousel to facilitate storing and releasing of said releasable items.

2. The apparatus as defined in claim 1, wherein said releasable items are one of pills, capsules, tables, medications, and drugs.

3. The apparatus as defined in claim 1, wherein said case is translucent.

4. The apparatus as defined in claim 1, further comprising a releasing engine carried by said housing for rotating said carousel so that said release openings of said carousel register in sequence with said discharge opening of said case.

5. The apparatus as defined in claim 1, wherein said cartridge and said housing are configured to release said releasable items by force of gravity.

6. The apparatus as defined in claim 1, wherein said compartments further includes at least two side walls for retaining said items in said circular array about said central axis of rotation of said carousel.

7. The apparatus as defined in claim 1, further comprising a user interface to interact with a user to facilitate releasig releasable items, said user interface comprising one of a display, button, audio speakers and light components.

8. The apparatus as defined in claim 1, wherein said carousel further includes radially extending tabs to facilitate indexing said compartments of said carousel and aligning said discharge opening witch said circular array of compartmens for registering with said release openings of each of said compartments in sequence as said carousel rotates.

9. The apparatus as defined in claim 1, wherein said cartridge further includes at least one locking arm that operatively couple with said carousel to facilitate aligning said discharge opening with said release opening.

10. The apparatus as defined in claim 1, wherein said case further includes an inner ring that facilitates positioning said carousel in said case about a central axis of rotation of said carousel and rotating said carousel for releasing said releasable items.

11. The apparatus as defined in claim 1, wherein said case includes an electronic chip, said chip being comprised of programmable readable memory that contains one of medication data, user identification data, releasing unit identification data, facility identification data and releasing activity data.

12. The apparatus as defined in claim 1, wherein said cartridge further includes a partitioning insert being coupled to said carousel such that said releasable items are positioned to the outer radius of said carousel.

13. The apparatus as defined in claim 1, further comprising a cartridge lock that locks said cartridge when said cartridge slides into said cartridge slot of said housing.

14. A releasing apparatus for releasing releasable items in sequence, said apparatus comprising:
housing defining plurality of cartridge slots;
at least one cartridge for insertion into at least one of said cartridge slots, each of said cartridge including a case and a carousel rotatably received in said case about a central axis of rotation;
said carousel comprising multiple compartments arranged in a circular array about the central axis of rotation of said carousel for storing the releasable items, each compartment having a release opening;
said case defining a discharge opening in alignment with said circular array of compartments for registering with said release openings of each of said compartments in sequence as said carousel rotates; and a drawer that slides in and out of said apparatus so that said releasable items are released into said drawer when said drawer is in said apparatus and said releasable items are accessible when said drawer is slid out of said apparatus.

15. A method for facilitating releasing releasable items from a releasing unit, said method comprising the steps of:
verifying whether a cartridge is authorized for usage with a releasing unit;
gathering data corresponding to said releasable items from said cartridge;
determining whether to release said items to a user in accordance with said items data; and
rotating a carousel in said cartridge such that said items in said carousel is released through a discharge opening of said cartridge, said cartridge comprising a bubble pack, said bubble pack being comprised of at least one sack, which is placed in said carousel to facilitate storing and releasing of said releasable items.

16. The method as defined in claim 15, wherein said step of verifying whether said cartridge is authorized usage with said releasing unit further comprising:
gathering data in an electronic chip coupled to said cartridge, said data corresponding to authorize information; and
determining whether said authorized data of said cartridge matches with identification data of said releasing unit.

17. The method as defined in claim 15, further comprising interfacing with a user by one of a display button, audio speakers, light components and pagers far releasing said releasable items.

18. The method as defined in claim 15, further comprising determining the availability of said releasable items cartridge.

19. The method as defined in claim 15, further comprising verifying access information to release said releasable items from said releasing unit.

20. The method as defined in claim 15, further comprising verifying whether to re-release said releasable items.

21. The method as defined in claim 15, further comprising pausing the activities of said releasing unit.

22. The method as defined in claim 15, further comprising advancing said releasable items to a user.

23. The method as defined in claim 15, further comprising paging a person via a modem to notify said person to release said releasable items.

24. The method as defined in claim 15, further comprising gathering said releasable items data and data corresponding to the activities of said items and send said items-activities data via a network and/or telephone line.

25. The method as defined in claim 15, further comprising recording data corresponding to the activities of said items in a memory in one of said cartridge and said releasing unit, wherein said activities data is sent to a central-computing device via a network and/or telephone line, wherein said central-computing device provides a database of said activities data to a provider i.e., pharmacist.

26. A method for facilitating releasing releasable items from a releasing unit said method comprising the steps of:
verifying whether a cartridge is authorized for usage with a releasing unit;
gathering data corresponding to said releasable items from said cartridge;
determining whether to release said items to a user in accordance with said items data;
rotating a carousel in said cartridge such that said items in said carousel is released through a discharge opening of said cartridge; and
releasing said items in a drawer and opening said drawer to obtain said items.

27. A releasing unit manager for enabling releasing releasable items, the manager stored on a computer-readable medium; the manager comprising:
logic configured to verify whether a cartridge is authorized for usage with a releasing unit;
logic configured to gather data corresponding to said releasable items front said cartridge;
logic configured to determine whether to release said releasable items to a user in accordance with said releasable items data; and
logic configured to rotate a carousel in said cartridge such that said items in said carousel is released through a discharge opening of said cartridge, said cartridge comprising a bubble pack, said bublepack being comprised of at least one sack, which is placed in said cartridge to facilitate storing and releasing of said releasable items.

28. The manager as defined in claim 27, wherein said logic configured to verify whether said cartridge is authorized for usage with said releasing unit further comprising:
logic configured to gather data in an electronic chip coupled to said cartridge, said data corresponding to authorize information; and logic configured to determine whether said authorized data of said cartridge matches with identification data of said releasing unit.

29. The manager as defined in claim 27, further comprising logic to determine the availability of releasable items in a cartridge.

30. The manager as defined in claim 27, further comprising the logic to verify access information to release the releasable items to a user.

31. The manager as defined in claim 27, further comprising the logic to verify whether to release the releasable items.

32. The manager as defined in claim 27, further comprising logic to pause the activities of the releasing unit.

33. The manager as defined in claim 27, further comprising logic to advance the releasable items to a user.

34. The manager as defined in claim 27, further comprising logic to page a person in order to notify the person to release the releasable items.

35. The manager as defined in claim 27, further comprising gathering the releasable items information and information corresponding to the activities of the items and send the releasable items activities information via a network and/or telephone line.

36. The method as defined in claim 27, further comprising logic to record data corresponding to the activities of said items in a memory in one of said cartridge and said releasing unit, wherein said activities data is sent to a central-computing device via a network and/or telephone line, wherein said central-computing device provides a database of said activities data to a provider, i.e., pharmacist.

37. A medication releasing system comprising:
a plurality of cartridge wherein a quantity of medication tablets are disposed, said cartridge being programed with encoded data for said medication tablets, said cartridge comprising a bubble pack, said buble pack being comprised of at least one sack, which is placed in said cartridge to facilitate storing and releasing of said medication tablets;
a releasing unit including a plurality of slots formed therein and configured to receive said cartridge in operative engagement;
a plurality of interfacing devices integrated into said releasing unit capable of raiding said encoded data and generating a digital signal in response thereto;
a processor being operatively connected to said interfacing devices capable of receiving said digital signal being programmable to transmit data via a modern and telephone lines to a pharmacist at a remote monitoring computer after said cartridge has been accessed a predetermined number of times; and
a user interface device integrated into said storing means and operatively connected to said microprocessing means enabling a user to enter a programmed pass code to actuate said cartridge to obtain a predetermined dosage of medication.

38. A releasing apparatus for releasing releasable items in sequence, said apparatus comprising:
a housing defining a plurality of cartridge slots;
at least one cartridge for insertion into at least one of said cartridge slots; and
a bubble pack being comprised of at least one sack, which are placed in said cartridge to facilitate storing and releasing of said releasable items.

39. The apparatus as defined in claim 38, wherein each of said cartridges including a case and a carousel rotatably received in said case about a central axis of rotation, said carousel comprising at least one compartment arranged in a circular array about the central axis of rotation of said carousel for storing the releasable items, each compartment having a release opening, said case defining a discharge opening in alignment with said circular array of compartments for registering with said release openings of each of said compartments in sequence as said carousel rotates.

40. The apparatus as defined in claim 39, wherein said at least one sack of said bubble pack is placed in said at least one compartment arranged in said circular array about said central, axis of rotation said carousel to facilitate storing and releasing of said releasable items.

41. The apparatus as defined in claim 40, further comprising a releasing engine carried by said housing for rotating said carousel so that said release openings of said carousel register in sequence with said discharge opening of said case.

42. The apparatus as defined in claim 40, wherein said compartments further include at least two said walls for retaining said items in said circular array about said central axis of rotation of said carousel.

43. The apparatus as defined in claim 40, wherein said carousel further includes radially extending tabs to facilitate indexing said compartments of said carousel and aligning said discharge opening with said circular array of compartments for registering with said release openings of each of said compartments in sequence as said carousel rotates.

44. The apparatus as defined in claim 40, wherein said cartridge further includes at least one locking arm that operatively couple with said carousel to facilitate aligning said discharge opening with said release opening.

45. The apparatus as defined in claim 40, wherein said case further includes an inner ring that facilitates positioning said carousel in said case about a central axis of rotation of said carousel and rotating said carousel for releasing said releasable items.

46. The apparatus as defined in claim 40, wherein said case includes an electronic chip, said chip being comprised of programmable readable memory that contains one of medication data, user identification data, releasing unit identification data, facility identification data and releasing activity data.

47. The apparatus as defined in claim 40, wherein said cartridge further includes a partitioning insert being coupled to said carousel such that said releasable items arc positioned to the outer radius of said carousel.

48. The apparatus as defined in claim 38, wherein said cartridge and said housing are configured to release said releasable items by force of gravity.

49. The apparatus as defined in claim 38, further comprising a user interface to interact with a user to facilitate releasing releasable items, said user interface comprising one of a display, button, audio speakers and light components.

* * * * *